US009750723B2

(12) United States Patent
McCall et al.

(10) Patent No.: US 9,750,723 B2
(45) Date of Patent: Sep. 5, 2017

(54) PREVENTION AND TREATMENT OF NON-ALCOHOLIC FATTY LIVER DISEASE

(71) Applicant: Ohio University, Athens, OH (US)

(72) Inventors: Kelly D. McCall, Athens, OH (US);
Frank L. Schwartz, Vienna, WV (US);
Douglas J. Goetz, Athens, OH (US);
Ramiro Malgor, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 15/032,508

(22) PCT Filed: Oct. 31, 2014

(86) PCT No.: PCT/US2014/063458
§ 371 (c)(1),
(2) Date: Apr. 27, 2016

(87) PCT Pub. No.: WO2015/066490
PCT Pub. Date: May 7, 2015

(65) Prior Publication Data
US 2016/0256439 A1 Sep. 8, 2016

(51) Int. Cl.
*A61K 31/415* (2006.01)
*A61K 31/4184* (2006.01)
*A61K 31/4164* (2006.01)
*C07D 233/84* (2006.01)
*A61K 45/06* (2006.01)

(52) U.S. Cl.
CPC ...... *A61K 31/4184* (2013.01); *A61K 31/4164* (2013.01); *A61K 45/06* (2013.01); *C07D 233/84* (2013.01)

(58) Field of Classification Search
CPC .................................................. A61K 31/415
USPC ........................................................ 514/401
See application file for complete search history.

(56) References Cited

U.S. PATENT DOCUMENTS

| 4,734,421 | A | 3/1988 | Hammond et al. |
| 5,162,360 | A | 11/1992 | Creswell et al. |
| 5,556,754 | A | 9/1996 | Singer et al. |
| 6,365,616 | B1 | 4/2002 | Kohn et al. |
| 6,465,472 | B1 | 10/2002 | Upasani et al. |
| 6,924,274 | B2 | 8/2005 | Lardy et al. |
| 7,928,132 | B2 | 4/2011 | Kohn et al. |
| 2005/0209295 | A1 | 9/2005 | Kohn et al. |
| 2008/0171700 | A1 | 7/2008 | Nilsson et al. |
| 2012/0238610 | A1 | 9/2012 | Kohn et al. |

FOREIGN PATENT DOCUMENTS

| AU | 2005275023 B2 | 3/2012 |
| EP | 692483 A1 | 1/1996 |
| WO | 9723200 A1 | 7/1997 |
| WO | 9852558 A1 | 11/1998 |
| WO | 9932106 A1 | 7/1999 |
| WO | 9932110 A1 | 7/1999 |
| WO | 9932111 A1 | 7/1999 |
| WO | 9932455 A1 | 7/1999 |
| WO | 0012175 A2 | 3/2000 |
| WO | 0025756 A2 | 5/2000 |
| WO | 2004017962 A2 | 3/2004 |
| WO | 2005094819 A1 | 10/2005 |
| WO | 2006019962 A1 | 2/2006 |

OTHER PUBLICATIONS

International Preliminary Report on Patentability dated May 12, 2016 pertaining to International Application No. PCT/US2014/063458.
International Search Report pertaining to PCT/US2014/063458 with the filing date Oct. 31, 2014 (2 pgs.).
Written Opinion pertaining to PCT/US2014/063458 with the filing date Oct. 31, 2014 (6 pgs.).
Ohmori, et al., Synergy Between Interferon-y and Tumor Necrosis Factor-x in Transcriptional Activation is Mediated by Cooperation Between Signal Transducer and Activator of Transcription 1 and Nuclear Factor kB, The Journal of Biological Chemistry, 1997, pp. 14899-14907, vol. 23, The American Society of Biochemistry and Molecular Biology, Inc., Rockville, Maryland, USA.
Jiang, et al., Toll-Like Receptor 3-Mediated Activation of Nf-kB and IRF3 Diverges at Toll-IL-1 Receptor Domain-Containing Adapter Inducing IFN-b, Proceedings of the National Academy of Sciences, 2004, pp. 3533-3538, vol. 101, No. 10, The National Academy of Sciences of the USA.
Kohn, et al., Toll-Like Receptors in Nonimmune Cells and Environmental Induction of the Pathologic Expression of Innate Immunity and Autoimmune Inflammatory Diseases: A New Therapeutic Opportunity, Research Ohio, 2005, pp. 1-23, vol. 15, A joint publication of Ohio University College of Osteopathic Medicine and the Ohio Osteapathic Foundation, Ohio, USA.
Mundschau, et al., Platelet-Derived Growth Factor Signal Transduction Through the Interferon-Inducible Kinase PKR, The Journal of Biological Chemistry, 1995, pp. 3100-3106, vol. 270, No. 7, The American Society for Biochemistry and Molecular Biology, Inc., Rockville, Maryland, USA.
Ivanovic, et al., Acute-Phase Protein Expression in DMSO-Intoxicated Rats, Toxicology Letters, 2004, pp. 153-159, Elsevier Ireland Ltd., Ireland.
Kirchhoff, et al., NFkB Activation is Required for Interferon Regulatory Factor-1-Mediated Interferon B Induction, European Biochemical Societies, 1999, pp. 546-554, vol. 26, Blackwell Publishing Ltd., Oxford, United Kingdom.

(Continued)

*Primary Examiner* — Raymond Henley, III
(74) *Attorney, Agent, or Firm* — Dinsmore & Shohl LLP

(57) ABSTRACT

Methods for preventing, treating, and/or reducing the risk of developing non-alcoholic fatty liver disease in a subject in need thereof and pharmaceutical compositions for the prevention or treatment of non-alcoholic fatty liver disease. The methods include administering a therapeutically effective amount of phenylmethimazole, methimazole derivatives, and/or tautomeric cyclic thiones to the subject. The pharmaceutical composition includes phenylmethimazole, methimazole derivatives, and/or tautomeric cyclic thiones formulated for administration to a subject for the prevention or treatment of non-alcoholic fatty liver disease.

20 Claims, 4 Drawing Sheets

(56) References Cited

OTHER PUBLICATIONS

Jones, Reuben G., Studies on Imidazole Compounds. I. A Synthesis of Imidazoles with Functional Groups in the 2-Position, J. Am. Chem. So., Feb. 1949, vol. 71, pp. 383-386.
Luscinskas, F.W., et al., 1996. Endothelial-dependent mechanisms in chronic inflammatory leukocyte recruitment. Annu. Rev. Med. Vo. 47, pp. 413-421.
Panes et al. 1999. Leukocyte-Endothelial Cell Adhesion: Avenues for Therapeutic Intervention. British Journal of Pharmacology, vol. 126, pp. 537-550.
Bevilacqua, M. P. 1991 Endothelial-Leukocyte Adhesion Molecules. Annu. Rev. Immunol. 11 :767-804.
Schindler, U., et al. 1994. Three NF-kappa B Binding Sites in the Human E-Selectin Gene Required for Maximal Tumor Necrosis Factor Alpha-Induced Expression. Molecular and Cellular Bioilogy, vol. 14, No. 9, pp. 5820-5831. American Society of Microbilogy.
Neish et al. 1992. Functional Analysis of the Human Vascular Cell Adhesion Molecule 1 Promoter. J Exp. Med., vol. 176, pp. 1583-1593, The Rockefeller University Press.
Neish et al. 1995. Sp1 is a Component of the Cytokine-Inducible Enhancer in the Promoter of Vascular Cell Adhesion Vlolecule-1. The Journal of Biological Chemistry, vol. 270, pp. 28903-28909.
Neish et al. 1995. Endothelial Interferon Regulatory Factor 1 Cooperates With NF-Kappa B as a Transcriptional Activator of Vascular Cell Adhesion Molecule, Molecular and Cellular Biology, May 1995, pp. 2258-2569, vol. 15, vol. 5, American Society of Microbilogy.
Ledebur et al. 1995 Transcriptional Regulation of the Intercellular Adhesion Molecule-1 Gene by Inflammatory Cytokines in Human Endothelial Cells. Essential Roles of a Variant NF-Kappa B Site and P65 Homodimers. Journal of Biological Chemistry, vol. 270, pp. 933-943, vol. 270. The American Society of Biochemistry and Molecular Biology, Inc., USA.
Munoz et al. 1996. Transcriptional Up-Regulation of Intracellular Adhesion Molecule-1 in Human Endothelial Cells by the Antioxidant Pyrrolidine Dithiocarbamate Involves the Activation of Activating Protein-1. The Journal of Immunology, vol. 157, pp. 3587-3597, The American Association of Immunologists.
May et al. 1998. Signal Transduction Through NF-Kappa B. Immunology Today vol. 19, pp. 80-88, Elsevier Science Ltd.
Pierce et al. 1996. Salicylates Inhibit I Kappa B-Alpha Phosphorylation, Endothelial-Leukocyte Adhesion Molecule Expression, and Neutrophil Transmigration. Journal of Immunology, vol. 156, pp. 3961-3969.
Pierce et al. 1997. Novel Inhibitors of Cytokine-Induced Ikba Phosphorylation and Endothelial Cell Adhesion Molecule Expression Show Anti-Inflammatory Effects in Vivo. Journal of Biological Chemistry, vol. 272, pp. 21096-21103.
Umetani et al. 2000. A Novel Cell Adhesion Inhibitor, K-7174, Reduces the Endothelial VCAM-1 Induction by Inflammatory Cytokines, Acting Through the Regulation of GAT A. Biochemical and Biophysical Research Communications, vol. 272, pp. 370-374, Academic Press.
Dagia et al. 2003. A Proteasome Inhibitor Reduces Concurrent, Sequential and Long Term IL-1.Beta. and TNF-.Alpha. Induced Endothelial Cell Adhesion Molecule Expression and Adhesion. Am. J. Phys. Cell Physiol., pp. C813-C822, The American Physiological Society.
Carlos et al. 1991. Human Monocytes Bind to Two Cytokine-Induced Adhesive Ligands on Cultured Human Endothelial Cells: Endothelial-Leukocyte Adhesion Molecule-1 and Vascular Cell Adhesion Molecule-1. Blood, vol. 77, pp. 2266-2271, The American Society of Hematology.
Alon et al. 1994. Distinct Cell Surface Ligands Mediate T Lymphocyte Attachment and Rolling on Pand E-Selectin Under Physiological Flow. The Journal of Cell Biology, vol. 127, pp. 1485-1495.
Alon et al. 1995. The Integrin VLA-4 Supports Tethering and Rolling in Flow on VCAM-1. The Journal of Cell Biology. vol. 128, pp. 1243-1253, The Rockefeller University Press.
Ochi et al. 2002. Hyperosmotic Stimuli Inhibit VCAM-1 Expression in Cultured Endothelial Cells Via Effects on Interferon Regulatory Factor-1 Expression and Activity, Eur. J. Immunol., vol. 32, pp. 1821-1831, Wiley-VCH Verlag GmbH, Weinheim, Germany.
Ahmad et al. 1998. Role of Activating Protein-1 in the Regulation of the Vascular Cell Adhesion Molecule-1 Gene Expression by Tumor Necrosis Factor-Alpha. Journal of Biological Chemistry, vol. 273, pp. 4616-4621.
Umetani et al. 2001. Function of GAT A Transcription Factors in Induction of Endothelial Vascular Cell Adhesion Molecule-1 by Tumor Necrosis Factor-Alpha. Arterioscler Thromb. Basc. Biol., pp. 917-922.
Kjellin et al. 1969. Tautomeric Cyclic Thiones. Part III. Preparation of N- and S-Methyl Derivatives of Some Azoline-2-Thiones. Acta Chemica Scandanavica 23: 2879-2887.
Calvey et al., J. Invest. Surg. (Mar.-Apr. 2007), 20(2), pp. 71-85.
Carlos, T. M., and J. M. Harlan. 1994. Leukocyte-Endothelial Adhesion Molecules. Blood 84:2068-2101.
Springer, T. A. 1994. Traffic Signals for Lymphocyte Recirculation and Leukocyte Emigration: The Multistep Paradigm Cell 76:301-314.
Dagia, N. M., N. Harii, A. E. Meli, X. Sun, C. J. Lewis, L. D. Kohn, and D. J. Goetz. 2004. Phenyl Methimazole Inhibits Tnfa-Induced VCAM-I Expression in an IFN Regulatory Factor-I-Dependent Manner and Reduces Monocytic Cell Adhesion to Endothelial Cells—J Immunol 173:2041-2049.
Yamamoto, M., S. Sato, K. Mori, K. Hoshino, O. Takeuchi, K. Takeda, and S. Akira. 2002. Cutting Edge: A Novel Tolvil-1 Receptor Domain-Containing Adapter That Preferentially Activates the IFN-Beta Promoter in the Toll-Like Receptor Signaling. J Immunol 169: 6668-6672.
Moutaery, Ahmed Al, Methimazole Prevents Stress and Chemical Induced Gastropathy in Rats, Exp Toxic Pathol. 2003, 55: pp. 277-285; http://www.elsevier-deutschland.de.
Gantner, et al., Collaborative Induction of Inflammatory Responses by Dectin-1 and Toll-Like Receptor 2, The Journal of Experimental Medicine, 2003, vol. 197, No. 9, pp. 1107-1117, USA.
Jones, et al., Differential Roles of Toll-Like Receptors in the Elicitation of Proinflammatory Responses by Macrophages, Ann Rheum Dis 2001, vol. 60, pp. iii6-iii12, Boston, MA, USA.
Devendra, et al., Interferon Alpha-A Potential Link in the Pathogenesis of Viral-Induced Type 1 Diabetes and Autoimmunity, Clinical Immunology, 2004, pp. 225-233, vol. 111, Elsevier, USA.
Mozes, et al., Spontaneous Autoimmune Disease in (NZB X NZW)F1 Mice is Ameliorated by Treatment with Methimazole, Journal of Clinical Immunology, 1998, pp. 106-113, vol. 18, No. 2, Plenum Publishing Company, New York, USA.
Luscinskas, et al., Monocyte Rolling, Arrest and Spreading on IL-4-Activated Vascular Endothelium Under Flow is Mediated via Sequential Action of L-Selectin, B1-Integrins, and B2-Integrins, The Journal of Cell Biology, 1994, pp. 1417-1427, vol. 125, No. 6, The Rockefeller University Press, New York, USA.
Napolitano, et al., High Glucose Levels Increase Major Histocompatibility Complex Class I Gene Expression in Thyroid Cells and Amplify Interferon-y Action, Endocrinology, 2002, pp. 1008-1017, vol. 143, No. 3, USA.
Hemmi, et al., Small Anti-Viral Compounds Activate Immune Cells via the TLR7 MyD88-Dependent Signaling Pathway, Department of Host Defense Research Institute for Microbial, Osaka University, 2002, pp. 196-200, vol. 3, No. 2, Nature Publishing Group, California, USA.
Oshiumi, et al., TIR-Containing Adapter Molecule (TICAM)-2, A Bridging Adapter Recruiting to Toll-Like Receptor 4 TICAM-1 That Induces Interferon-B, The Journal of Biological Chemistry by the American Society for Biochemistry and Molecular Biology, Inc., 2003, pp. 49751-49762, vol. 278, No. 50, http://www.jbc.org, USA.
Ishii, et al., Genomic DNA Released by Dying Cells Induces the Maturation of APCs1,2, Nature Immunology, 2001, pp. 2602-2607, vol. 167, The American Association of Immunologists, USA.
Suzuki, et al., Transfection of Single-Stranded Hepatitis A Virus RNA Activates MHC Class I Pathway, Clinical Exp. Immunology, 2002, pp. 234-242, vol. 127, Blackwell Science, Oxford, United Kindgom.

(56) References Cited

OTHER PUBLICATIONS

Eader, et al., Induction of Multiple Cytokine Gene Expression and IRF-1 mRNA by Flavone Acetic Acid in a Murine Macrophage Cell Line1, Cellular Immunology, 1994, pp. 211-222, vol. 157, Academic Press, Inc., Waltham, Massachusetts, USA.

Delgado, et al., Vasoactive Intestinal Peptide and Pituitary Adenylate Cyclase-Activating Polypeptide Prevent Inducible Nitric Oxide Synthase Transcription in Macrophages by Inhibiting NF-kB and IFN Regulatory Factor 1 Activation, The Journal of Immunology, 1999, pp. 4685-4696, vol. 162, The American Association of Immunologists, USA.

Fujimoto, et al., A Role for iNOS in Fasting Hyperglycemia and Impaired Insulin Signaling in the Liver of Obese Diabetic Mice, Diabetes, 2005, pp. 1340-1348, vol. 54, The American Diabetes Association, USA.

Servant, et al., Overlapping and Distinct Mechanisms Regulating IRF-3 and IRF-7 Function, Journal of Interferon and Cytokine Research, 2002, pp. 49-58, vol. 22, Mary Ann Liebert, Inc., New York, USA.

Horwitz, et al., Diabetes Induced by Coxsackie Virus: Initiation by Bystander Damage and Not Molecular Mimicry, Nature Medicine, 1998, pp. 781-785, vol. 4, No. 7, Nature Publishing Group, California, USA.

Yamamoto, et al., Essential Role for TIRAP in Activation of the Signalling Cascade Shared by TLR2 and TLR4, Nature, 2002, www.nature.com/nature, pp. 324-329, vol. 420, Nature Publishing Group, California, USA.

McCartney-Francis, et al ., Dysregulation of IFN-y Signaling Pathways in the Absence of TGF-b1, The Journal of Immunology, 2002, pp. 5941-5947, vol. 169, http://jimmunol.org, The American Association of Immunologists, Inc., USA.

Kamijo, et al., Requirement for Transcription Factor IRF-1 in NO Synthase Induction in Macrophages, Science, 1994, pp. 1612-1615, vol. 263, Journal Storage, USA.

Pine, et al., Tyrosine Phosphorylated p91 Binds to a Single Element in the ISGF2/IRF-1 Promoter to Mediate Induction by IFNx and IFNy, and is Likely to Autoregulate the p91, The EMBO Journal, 1994, pp. 158-167, vol. 13, No. 1, Oxford Press, New York, USA.

Nakazawa, et al., Complete Suppression of Insulitis and Diabetes in NOD Mice Lacking Interferon Regulatory Factor-1, Journal of Autoimmunity, 2001, pp. 119-125, vol. 17, Academic Press, Inc., Waltham, Massachusetts, USA.

Li, et al., Role of p38x Map Kinase in Type I Interferon Signaling, The Journal of Biological Chemistry, 2004, pp. 970-979, vol. 279, No. 2, The American Society of Biochemistry and Molecular Biology, Inc., Rockville, Maryland, USA.

PREVENTION AND TREATMENT OF NON-ALCOHOLIC FATTY LIVER DISEASE

CROSS REFERENCE TO RELATED APPLICATIONS

This application claims priority under 35 U.S.C. §119 to U.S. Provisional Patent Application No. 61/898,110, filed Oct. 31, 2013, entitled "Prevention and Treatment of Non-Alcoholic Fatty Liver Disease", the contents of which are hereby incorporated by reference in their entirety.

TECHNICAL FIELD

The present disclosure relates generally to the prevention and treatment of non-alcoholic fatty liver disease (hereinafter, "NAFLD"). More particularly, the present disclosure relates to one or more of methods for preventing NAFLD, methods of treating NAFLD, and pharmaceutical compositions for the prevention and/or treatment of NAFLD.

BACKGROUND

NAFLD is a form of fat-induced inflammation of the liver which is present throughout the industrialized world. The prevalence of NAFLD ranges from 10% to 24% in the general population and NAFLD is the leading cause of cirrhosis, chronic liver failure, liver transplantation, and primary hepatic cancers in the United States. NAFLD is associated with metabolic syndrome (e.g., obesity, diabetes mellitus, hyperlipidemia, and/or hypertension), certain medications (e.g., estrogens, coumadin, tamoxifen, valproic acid, methotrexate, isoniazid, corticosteroids, Vitamin A, troglitazone, I-Asparaginase, amiodarone, perhexiline, calcium channel blockers, and/or nucleoside analogues), Hepatitis C, nutritional risk factors (e.g., rapid weight loss, total parenteral nutrition, starvation, and/or protein-calorie malnutrition), certain surgical procedures (e.g., gastrointestinal surgery for obesity and/or extensive small-bowel resection), metabolic disorders (e.g., cystic fibrosis and/or abetalipoproteinemia), syndromes associated with obesity and insulin resistance (e.g., lipodystrophies, hypopituitarism, and/or Prader-Willi syndrome), and various other conditions. With particular regard to obesity (a feature of metabolic syndrome), NAFLD is observed in up 75% of obese persons.

While there are medications approved for treating diseases and conditions associated with NAFLD, there are currently no medications specifically approved for the treatment of NAFLD itself. As a result, treatment protocols are focused upon the associated conditions, such as metabolic syndrome. For example, conventional treatment of NAFLD may include weight loss, restricting dietary fat, administration of medications employed in the treatment of an associated condition (e.g., metformin and thiazolidinediones), and administration of medications employed in the treatment of hyperlipidemia (e.g., HMG-Co-A inhibitors). However, in addition to there being no standard treatment specific to NAFLD, many medications employed to treat conditions associated with NAFLD are hepatotoxic.

SUMMARY

The present disclosure is based on the unexpected discovery that phenylmethimazole (i.e., C10), methimazole derivatives, and tautomeric cyclic thiones can be used to prevent and/or treat NAFLD. Accordingly, provided herein is an entirely new paradigm for disease intervention. In some embodiments, provided are methods for treating NAFLD in a subject in need thereof. Such methods include administering a composition including a therapeutically effective amount of phenylmethimazole, methimazole derivatives, and/or tautomeric cyclic thione, or a pharmaceutically-acceptable salt or solvate thereof, or pharmaceutical compositions including the same, to the subject.

In some embodiments, also provided are methods for preventing or otherwise reducing the risk of developing NAFLD in a subject in need thereof. Such methods include administering a composition including a therapeutically effective amount of phenylmethimazole, methimazole derivatives, and/or tautomeric cyclic thiones, or a pharmaceutically-acceptable salt or solvate thereof, or pharmaceutical compositions including the same, to the subject.

In yet other embodiments, provided are pharmaceutical compositions for the prevention and/or treatment of NAFLD. Such anti-NAFLD agents include phenylmethimazole, methimazole derivatives, and tautomeric cyclic thiones, and/or are formulated for administration to a subject. In some embodiments, the provided anti-NAFLD agents are pharmaceutical compositions including phenylmethimazole, methimazole derivatives, and/or tautomeric cyclic thiones, or pharmaceutically-acceptable salts or solvates thereof, and one or more compounds effective in treating a NAFLD-associated disease or condition.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

Figure 1:
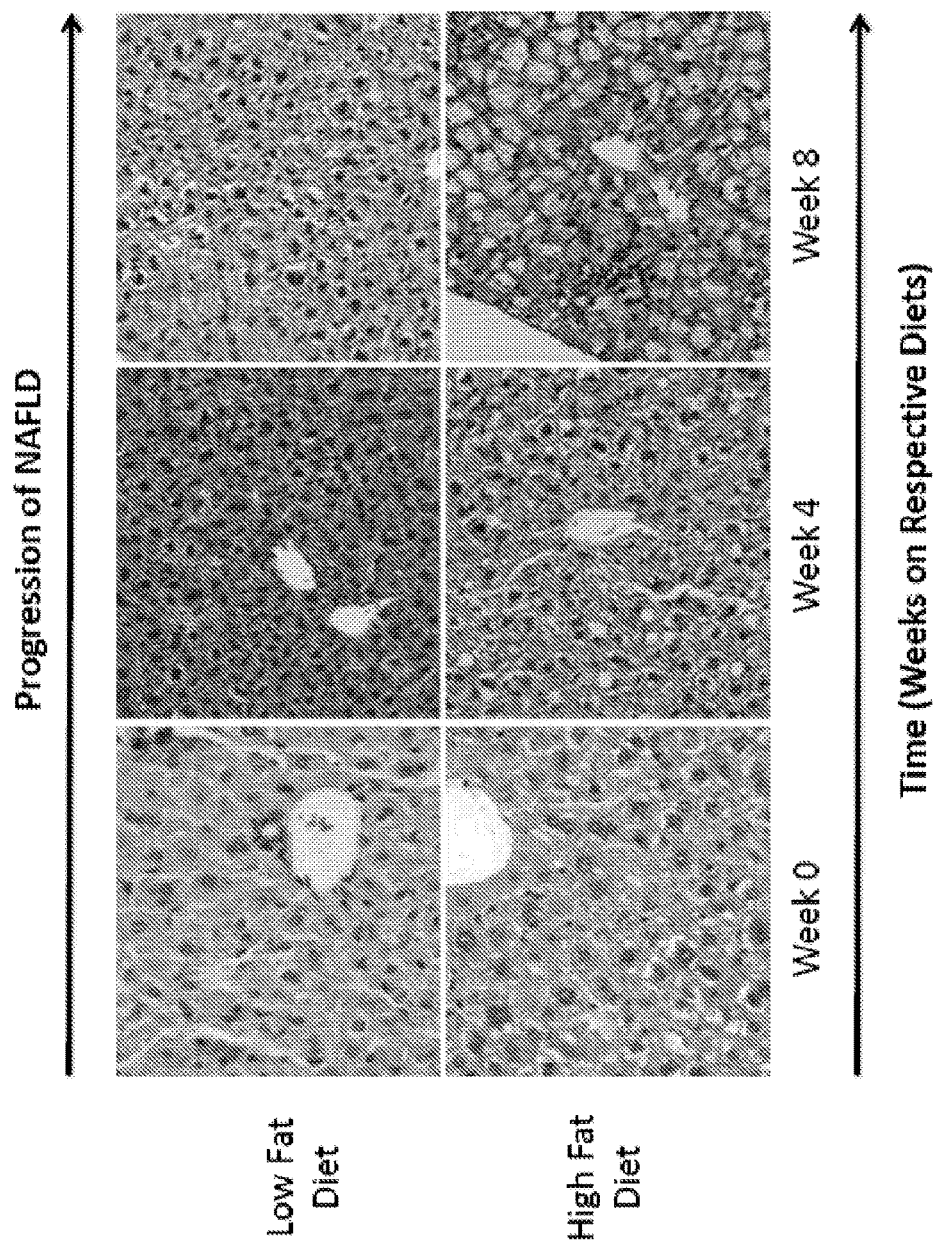
FIG. 1 is a micrograph of liver tissue harvested from C57BL/6J mice on a low fat diet and C57BL/6J mice on a high fat diet at 0 weeks, 4 weeks, and 8 weeks.

Skilled artisans appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments of the present disclosure.

DETAILED DESCRIPTION

The following terms are used in the present application:

The terms "prevent," "prevention," and "preventing," as used herein, refer to prophylactically avoiding or prolonging the development or acquisition of NAFLD. The terms "prevent," "prevention," and "preventing", as used herein, may also refer to reducing the risk of developing or acquiring NAFLD.

The terms "treat," "treatment," and "treating," as used herein, refer to alleviating, ameliorating, stabilizing, delaying onset, inhibiting progression of, or abrogating a disease, disorder, and/or symptoms thereof.

The terms "non-alcoholic fatty liver disease" and "NAFLD" as used herein, refer to a chronic disease or disorder wherein excessive fat (e.g., triglycerides and/or free fatty acids) accumulates in a liver cell, liver tissue, and/or the liver of subjects who drink little or no alcohol. Excessive fat may accumulate in a liver cell, liver tissue, and/or the liver of subjects via steatosis, which may trigger inflammatory processes therein. NAFLD includes a spectrum of stages, generally including: steatosis, non-alcoholic steatohepatitis (hereinafter, "NASH"), fibrosis, and cirrhosis. The spectrum of stages increase in severity from steatosis to NASH to fibrosis to cirrhosis.

The term "steatosis" as used herein, refers to a stage of NAFLD involving the process of abnormal retention or accumulation of fat within a liver cell, liver tissue, and/or the liver. During steatosis, a liver cell accumulates fat vacuoles (e.g., liposomes) around the nucleus. In an early stage of steatosis, a liver cell may accumulate multiple fat vacuoles which do not displace the nucleus (i.e., microvesicular fatty change). However, in a later stage of steatosis, the accumulated fat vacuoles may increase in size, causing displacement of the nucleus toward the periphery of the liver cell (i.e., macrovesicular fatty change). Steatosis is the first stage of NAFLD.

The terms "non-alcoholic steatohepatitis" and "NASH" as used herein, refer to a stage of NAFLD involving abnormal retention or accumulation of fat within a liver cell, liver tissue, and/or the liver accompanied by lymphocytic migration into the liver, resulting in inflammation thereof. NASH is the second stage of NAFLD.

The term "fibrosis" as used herein, refers to a later stage of NAFLD wherein liver cell death and inflammation trigger stellate cell formation and excess fibrous connective tissue formation within liver tissue, the liver, hepatic sinusoids and/or hepatic veins. Fibrosis may lead to cirrhosis of the liver. Fibrosis is the third stage of NAFLD.

The term "cirrhosis" as used herein, refers to a stage of NAFLD involving replacement of liver tissue by fibrosis, scar tissue, and/or regenerative hepatic nodules, leading to the loss of function of liver tissue and/or the liver. Cirrhosis may lead to liver failure, coma, and/or death of the subject. Cirrhosis is the fourth stage of NAFLD.

Depending upon the context of use, the term "subject in need thereof" as used herein, refers to a subject at risk for developing NAFLD, a subject exhibiting symptoms associated with NAFLD, and/or a subject having NAFLD. One example of a subject at risk for developing NAFLD includes, but should not be limited to, a subject having a disease or condition associated with NAFLD. Examples of diseases or conditions associated with NAFLD include, but should not be limited to, a subject having features of metabolic syndrome (e.g., obesity, diabetes mellitus, hyperlipidemia, and/or hypertension); a subject taking certain medications (e.g., estrogens, coumadin, tamoxifen, valproic acid, methotrexate, isoniazid, corticosteroids, Vitamin A, troglitazone, I-Asparaginase, amiodarone, perhexiline, calcium channel blockers, and/or nucleoside analogues); a subject having Hepatitis C; a subject having elevated liver enzymes and/or abnormal liver function tests; a subject having certain nutritional risk factors (e.g., rapid weight loss, total parenteral nutrition, starvation, and/or protein-calorie malnutrition); a subject having undergone certain surgical procedures (e.g., gastrointestinal surgery for obesity and/or extensive small-bowel resection); a subject having a metabolic disorder (e.g., cystic fibrosis and/or abetalipoproteinemia); a subject having a syndrome associated with obesity and/or insulin resistance (e.g., lipodystrophies, hypopituitarism, and/or Prader-Willi syndrome); and a subject having various other conditions (e.g., inflammatory bowel disease, small-bowel diverticulosis, viral infection, and/or exposure to petrochemicals and/or toxic mushrooms). Examples of symptoms associated with NAFLD include, but should not be limited to, fatigue, pain in the upper right abdomen, and weight loss. With regard to a subject having NAFLD, diagnosis of NAFLD may be performed using standard diagnostic testing techniques for NAFLD, such as are known to those of ordinary skill in the art. Examples of standard diagnostic testing techniques for NAFLD include, but should not be limited to, molecular determinations including blood tests (e.g., liver function tests including tests of liver enzymes and/or triglyceride quantification); microscopic determinations including imaging procedures (e.g., ultrasound, computerized tomography scan and/or magnetic resonance imaging); and microscopic determinations including liver tissue testing (e.g., liver biopsy). In some embodiments, NAFLD may be visualized macroscopically via the naked eye.

The term "therapeutically effective amount" as used herein, refers to an amount necessary or sufficient to realize a desired biologic effect. The therapeutically effective amount may vary depending on a variety of factors known to those of ordinary skill in the art, including but not limited to, the particular composition being administered, the activity of the composition being administered, the size of the subject, the sex of the subject, the age of the subject, the general health of the subject, the timing and route of administration, the rate of excretion, the administration of additional medications, and/or the severity of the disease or disorder being prevented and/or treated. In some embodiments, the term therapeutically effective amount refers to the amount of phenylmethimazole, methimazole derivatives, and/or tautomeric cyclic thiones necessary or sufficient to prevent NAFLD or treat NAFLD.

The terms "phenylmethimazole" and "C10" as used herein, refer to 5-phenylmethimazole having the chemical formula $C_{10}H_{10}N_2S$ and having the following chemical structure:

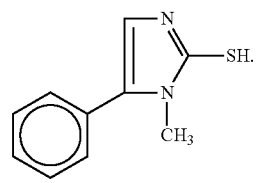

Phenylmethimazole also includes pharmaceutically acceptable salts or solvates thereof. Phenylmethimazole (i.e., 5-phenylmethimazole) having a molecular weight of about 190.27 and a boiling point of 168°-173°, may be synthesized using techniques known to those skilled in the art. For example, phenylmethimazole may be synthesized using the methods described by R. G. Jones, J. Am. Chem. So., 1949, 71: 383-386 and by Kohn et al. in U.S. Pat. No. 6,365,616, the contents of which are incorporated by reference herein.

The term "methimazole derivatives" as used herein, refers to the compositions having the structural formulae disclosed in U.S. Pat. No. 6,365,616 and U.S. Pub. No. 2012/0238610, the contents of which are incorporated by reference herein. More specifically, methimazole derivatives are limited to the compositions having the following general structural formulae:

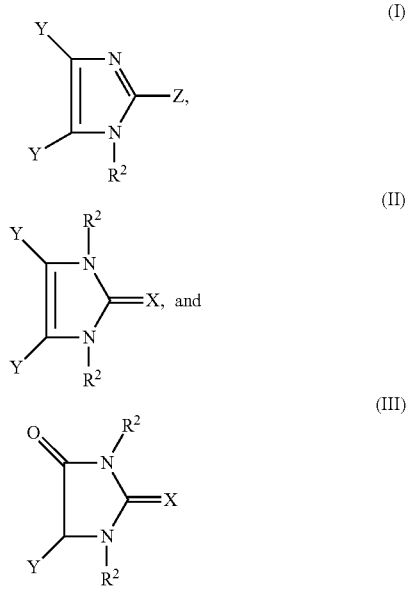

or pharmaceutically-acceptable salts or solvates thereof, in which: Y is independently selected from H, $C_1$-$C_4$ alkyl, $C_1$-$C_4$ substituted alkyl, —$NO_2$, and a phenyl moiety having the following structural formula:

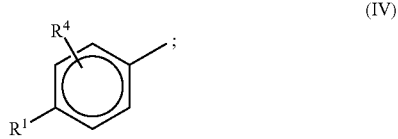

no more than one Y group may be the phenyl moiety having Formula (IV); $R^1$ is independently selected from H, —OH, halogens, $C_1$-$C_4$ alkyl, $C_1$-$C_4$ substituted alkyl, $C_1$-$C_4$ ester and $C_1$-$C_4$ substituted ester; $R^2$ is independently selected from H, $C_1$-$C_4$ alkyl and $C_1$-$C_4$ substituted alkyl; $R^3$ is independently selected from H, $C_1$-$C_4$ alkyl, $C_1$-$C_4$ substituted alkyl and —$CH_2Ph$ (wherein Ph is phenyl); $R^4$ is independently selected from H, $C_1$-$C_4$ alkyl, and $C_1$-$C_4$ substituted alkyl; X is independently S or O; Z is independently selected from $C_1$-$C_4$ alkyl, —$SR^3$, —$S(O)R^3$ and —$OR^3$; at least two of the $R^2$ and $R^3$ groups are $C_1$-$C_4$ alkyl when Y is not the phenyl moiety having Formula (IV); and at least one Y is —$NO_2$ when Z is alkyl.

In particular embodiments, Y is independently selected from H, the phenyl moiety having Formula (IV), and —$NO_2$. In some particular embodiments, $R^1$ is independently selected from H, —OH, halogens, —$OOCCH_2M$ (wherein M is H or a halogen). In further embodiments, $R^1$ is H. In still other particular embodiments, $R^2$ is independently selected from H, $C_1$-$C_4$ alkyl, and $C_1$-$C_4$ substituted alkyl. In further embodiments, at least one $R^2$ is methyl. In some particular embodiments, $R^3$ is independently selected from H and $C_1$-$C_4$ alkyl. In further embodiments, $R^3$ is $C_1$-$C_4$ alkyl, such as, e.g., methyl. In other particular embodiments, $R^4$ is H. In still other particular embodiments, Z is independently selected from —$SR^3$, —$OR^3$, and —$S(O)R^3$. In further embodiments, Z is independently selected from —$SR^3$ and —$OR^3$. In yet further embodiments, Z is —$SR^3$. In some particular embodiments, at least two of $R^2$ and $R^3$ are $C_1$-$C_4$ alkyl when Y is not the phenyl moiety having Formula (IV). In other particular embodiments, at least one Y is —$NO_2$ when Z is $C_1$-$C_4$ alkyl.

The methimazole derivatives also include pharmaceutically acceptable salts thereof. The methimazole derivatives may be synthesized using techniques known to those skilled in the art. For example, representative methimazole derivatives may be synthesized using the following procedure: (a) appropriately substituted analogs of acetaldehyde are brominated in the 2-position by treatment with bromine and UV light, followed by formation of the corresponding diethylacetal using absolute ethanol; (b) the bromine is then displaced from this compound by treatment with anhydrous methylamine, or another suitable amine, in a sealed tube at about 120° for up to about 16 hours; (c) reaction of the resulting aminoacetal with potassium thiocyanate in the presence of hydrochloric acid, at steam bath temperatures overnight, provides the methimazole derivatives.

As used herein, the term "substituted alkyl" refers to alkyl and aryl groups which are substituted in one or more places with hydroxyl or alkoxyl groups, carboxyl groups, halogens, nitro groups, amino or acylamino groups, and combinations thereof. By way of example, substituted alkyl groups include $C_1$-$C_4$ hydroxyl and alkoxyl groups.

As used herein, the term "substituted ester" refers to ester groups which are substituted in one or more places with hydroxyl or alkoxyl groups, carboxyl groups, halogens, nitro groups, amino or acylamino groups, and combinations thereof.

As used herein, the terms "halo" and "halogens" refer to atoms selected from fluorine, chlorine, bromine and iodine.

As used herein, the term "pharmaceutically acceptable salts" refers to salts prepared from pharmaceutically acceptable non-toxic bases or acids including inorganic or organic bases and inorganic or organic acids. Salts derived from inorganic bases include: aluminum, ammonium, calcium, copper, ferric, ferrous, lithium, magnesium, manganic salts, manganous, potassium, sodium, zinc, and the like. In some embodiments, the salts derived from inorganic bases include: ammonium, calcium, magnesium, potassium, and sodium salts. Salts derived from pharmaceutically acceptable organic non-toxic bases include: salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When a compound is basic, salts may be prepared from pharmaceutically acceptable non-toxic acids, including inorganic and organic acids. Such acids include: acetic, benzenesulfonic, benzoic, camphor-sulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantoth-enic, phosphoric, succinic, sulfuric, tartaric, p-toluenesulfo-nic acid, and the like. In some embodiments, the acids include: citric, hydrobromic, hydrochloric, maleic, phos-phoric, sulfuric, and tartaric acids. Thus, representative pharmaceutically acceptable salts include, but are not lim-ited to, acetate, benzenesulfonate, benzoate, bicarbonate, bisulfate, bitartrate, borate, bromide, calcium edetate, cam-sylate, carbonate, chloride, clavulanate, citrate, dihydrochlo-ride, edetate, edisylate, estolate, esylate, fumarate, glu-ceptate, gluconate, glutamate, glycollylarsanilate, hexyl-resorcinate, hydrabamine, hydrobromide, hydrochloride, hydroxynaphthoate, iodide, isethionate, lactate, lactobion-ate, laurate, malate, maleate, mandelate, mesylate, methyl-bromide, methylnitrate, methylsulfate, monopotassium maleate, mucate, napsylate, nitrate, N-methylglucamine, oxalate, pamoate (embonate), palmitate, pantothenate, phos-phate/diphosphate, polygalacturonate, potassium, salicylate, sodium, stearate, subacetate, succinate, tannate, tartrate, teoclate, tosylate, triethiodide, trimethylammonium and val-erate. It will be understood that, as used herein, the com-pounds referred to are meant to also include the pharma-ceutically acceptable salts.

It is understood that certain embodiments herein encom-pass the use of pharmaceutically acceptable salts, pharma-ceutically acceptable solvates, or pharmaceutically accept-able salts solvated with pharmaceutically acceptable solvents. As used herein, the term "solvate" or "salt sol-vated" refers to a complex of variable stoichiometry formed by a solute and a solvent. In some embodiments, such solvents do not interfere with the biological activity of the solute. Examples of suitable solvents include, but are not limited to, water, methanol, ethanol and acetic acid. In illustrative embodiments, the solvent is a pharmaceutically acceptable solvent. Examples of suitable pharmaceutically acceptable solvents include, without limitation, water, etha-nol, and acetic acid. In particular embodiments, the solvent is water, providing a "hydrate."

The term "tautomeric cyclic thiones" as used herein, refers to the compositions having the general structural formulae disclosed in U.S. Pat. No. 6,365,616, U.S. Pub. No. 2012/0238610, and in Kjellin and Sandstrom, Acta Chemica Scandinavica, 23: 2879-2887 and 2888-2899 (1969), the contents of which are incorporated by reference herein. More specifically, tautomeric cyclic thiones are limited to the compositions having the following general structural formulae:

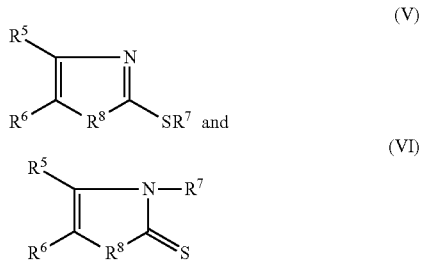

or pharmaceutically-acceptable salts or solvates thereof, in which: $R^5$ is independently selected from $CH_3$, Ph (wherein Ph is phenyl), and H; $R^6$ is independently selected from $CH_3$, H, and Ph (wherein Ph is phenyl); $R^7$ is independently selected from H and $CH_3$; and $R^8$ is independently selected from O, S, NH, and $NCH_3$. By way of example, a series of tautomeric cyclic thiones include oxazoline-, thiazoline-, and imidazoline-2-(3)-thiones, having methyl and phenyl groups in the 4 and 5 positions.

The tautomeric cyclic thiones may be synthesized using techniques known to those of ordinary skill in the art. For example, the synthesis of several tautomeric cyclic thiones is described in Kjellin and Sandstrom, Acta Chemica Scan-danavica 23: 2879-2887 (1969), the contents of which are incorporated by reference herein.

In particular embodiments, the methimazole derivatives and/or tautomeric cyclic thiones of Formulae (I)-(III) and/or (V)-(VI) include compounds having the following structural formulae:

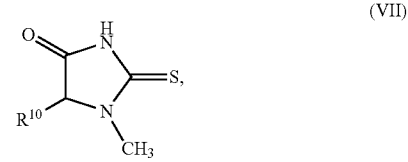

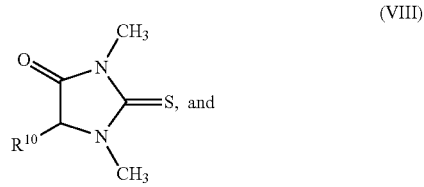

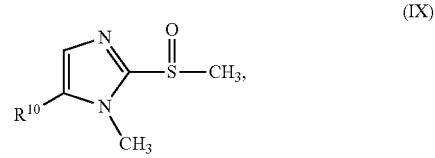

in which:

$R^{10}$ is independently selected from H, $NO_2$, Ph (wherein Ph is phenyl), 4-HOPh, and 4-halo-Ph.

In particular embodiments, the methimazole derivatives and/or tautomeric cyclic thiones of Formulae (I)-(III) and/or (V)-(VI) include compounds having the following structural formulae:

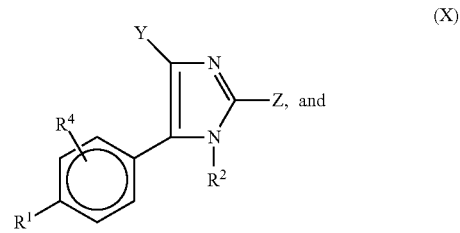

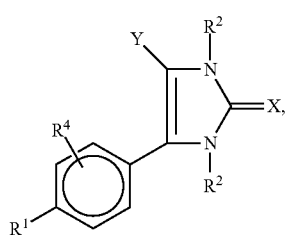

(XI)

in which:
Y is independently selected from H, $C_1$-$C_4$ alkyl, and $C_1$-$C_4$ substituted alkyl; $R^1$ is independently selected from H, —OH, halogens, $C_1$-$C_4$ alkyl, $C_1$-$C_4$ substituted alkyl, $C_1$-$C_4$ ester and $C_1$-$C_4$ substituted ester; $R^2$ is independently selected from H, $C_1$-$C_4$ alkyl, and $C_1$-$C_4$ substituted alkyl; $R^3$ is independently selected from H, $C_1$-$C_4$ alkyl, $C_1$-$C_4$ substituted alkyl, and —$CH_2Ph$ (wherein Ph is phenyl); $R^4$ is independently selected from H, $C_1$-$C_4$ alkyl, and $C_1$-$C_4$ substituted alkyl; X is selected from S and O; and Z is selected from —$SR^3$ and —$OR^3$.

In some particular embodiments, Y is H in the compounds of Formulae (X) and (XI). In other particular embodiments, $R^1$ is independently selected from H, —OH, halogens, and —$OOCCH_2M$ (wherein M is H or a halogen) in the compounds of formulae (X) and (XI). In other embodiments, at least one $R^2$ is methyl in the compounds of formulae (X) and (XI). In some embodiments, $R^3$ is independently selected from H and methyl in the compounds of formulae (X) and (XI). In other embodiments, $R^4$ is H in the compounds of formulae (X) and (XI). In still other embodiments, X is S in the compounds of formulae (X) and (XI). In still other particular embodiments, Z is —$SR^3$ in the compounds of formulae (X) and (XI).

In particular embodiments, the methimazole derivatives and/or tautomeric cyclic thiones of Formulae (I)-(III) and/or (V)-(VI) include compounds having the following Formulae:

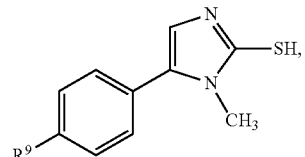

(XII)

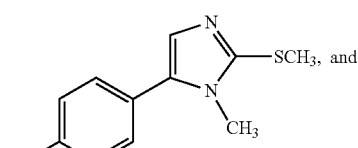

(XIII)

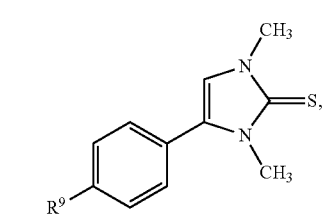

(XIV)

in which:
$R^9$ is independently selected from —OH, -M and —$OOCCH_2M$ (wherein M is a halogen).

Specific examples of methimazole derivatives and/or tautomeric cyclic thiones suitable for use in the methods described herein include the following compounds listed below in Table I:

TABLE I

Exemplary Methimazole Derivatives and/or Tautomeric Cyclic Thiones

| COMPOUND REFERENCE NUMBER | NAME/CHEMICAL FORMULA/PROPERTIES | STRUCTURE |
|---|---|---|
| 1 | 1-Methylimidazoe-2-thiol (Methimzaole) $C_4H_6N_2S$: 1-Methyl-2-mercaptoimidazole (i.e., MMI) | 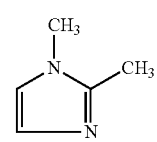 |
| 2 | 2-Methyl-5-nitro-1-imidazole ethanol (i.e., Metronidazole) $C_6H_9N_3O_3$; MW: 171.16 | 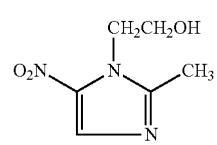 |
| 3 | 2-Mercaptoimidazole MW: 100.14 | 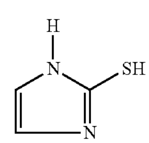 |

TABLE I-continued

Exemplary Methimazole Derivatives and/or Tautomeric Cyclic Thiones

| COMPOUND REFERENCE NUMBER | NAME/CHEMICAL FORMULA/PROPERTIES | STRUCTURE |
|---|---|---|
| 4 | 2-Mercaptobenzimidazole MW: 150.20 | 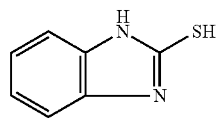 |
| 5 | 2-Mercapto-5-nitrobenzimidazole MW: 195.20 | 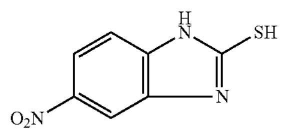 |
| 6 | 2-Mercapto-5-methylbenzimidazole MW: 164.3 | 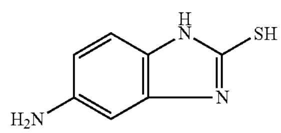 |
| 7 | S-Methylmethimazole $C_5H_8N_2S$; MW: 128.20 B.P. 48° @ 100 u (liq.) | 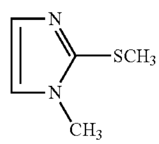 |
| 8 | N-Methylmethimazole $C_5H_8N_2S$; MW: 128.20 B.P. 188°-194° | 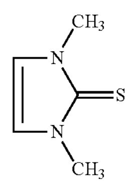 |
| 9 | 5-Methylmethimazole $C_5H_8N_2S$; MW: 128.20 B.P. 254°-255° | 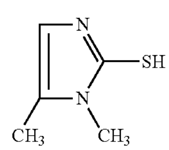 |
| 10 | 5-Phenylmethimazole $C_{10}H_{10}N_2S$; MW: 190.27 B.P. 168°-173° | 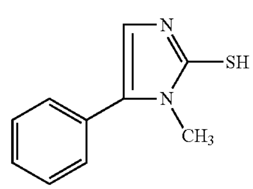 |
| 11 | 1-Methyl-2-Thiomethyl-5(4)nitroimidazole | 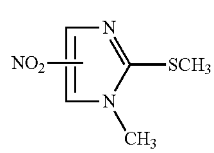 |

The term "excessive accumulation of fat" as used herein, refers to an amount of fat accumulation in a liver cell, liver tissue, and/or the liver which is greater than an amount of fat accumulation in a normal liver cell, liver tissue, and/or the liver in a subject who is not in need of treatment for NAFLD (i.e., a normal level). The determination of an excessive accumulation of fat may be accomplished via standard diagnostic testing techniques for NAFLD, as previously described. More specifically, in some embodiments, the determination of an excessive accumulation of fat may be accomplished via molecular determinations and/or microscopic determinations wherein an amount of fat in a liver cell, liver tissue, and/or the liver of a subject is assessed (such as, e.g., visually and/or quantifiably) as being greater than an amount of fat in a normal liver cell, liver tissue, and/or the liver of a subject who is not in need of treatment for NAFLD (i.e., a control or reference subject). In some embodiments, a sample of the liver cell, liver tissue, and/or the liver of the subject to be assessed (i.e., a biological sample) and a sample of the liver cell, liver tissue, and/or the liver of the control subject (i.e., a control sample) are provided for the determination of an excessive accumulation of fat.

The terms "fat" and "fat content" as used herein, respectively refer to triglycerides, free fatty acids, vacuoles of triglycerides, and/or vacuoles of free fatty acids which accumulate in a liver cell, liver tissue, and/or the liver.

The term "baseline level" as used herein, refers to a level of fat content in a liver cell, liver tissue, and/or the liver in a subject prior to administration of phenylmethimazole and/or other medications for preventing and/or treating NAFLD. The baseline level may be determined via molecular determinations and/or microscopic determinations (such as, e.g., visual and/or quantifiable determinations).

The term "normal level" as used herein, refers to a level of fat content in a normal liver cell, liver tissue, and/or the liver from a subject (i.e., a control subject) who is not in need of treatment for NAFLD. The normal level allows distinguishability between subjects suffering from a disease or condition and subjects not suffering from a disease or condition, e.g., NAFLD.

The term "pharmaceutically acceptable carrier" as used herein, refers to a pharmaceutically active compound and/or other ingredients for use in a pharmaceutical composition which are not deleterious to a subject receiving the pharmaceutical composition and/or which are suitable for use in contact with the tissues of humans and lower animals without undue toxicity, irritation, allergic response, and the like commensurate with a reasonable benefit/risk ratio.

The term "administration" as used herein, refers to systemic use, such as by injection (e.g., parenterally), intravenous infusion, suppositories and oral administration thereof, and/or to topical use of the phenylmethimazole, methimazole derivatives, tautomeric cyclic thiones, and pharmaceutical compositions including the same.

The term "compatible" as used herein, refers to components for use in a pharmaceutical composition which are capable of being comingled without interacting in a manner which would substantially decrease the efficacy of the pharmaceutically active compound under ordinary use conditions.

The terms "a," "an," and "the", as used herein, refer to "one or more." For example, reference to "a liver cell" may include both reference to a single liver cell and reference to a plurality of liver cells.

Embodiments of the present disclosure relate to methods for preventing and/or treating NAFLD and to pharmaceutical compositions for preventing and/or treating NAFLD. Embodiments of the methods for preventing and/or treating NAFLD will now be described in detail. Thereafter, embodiments of pharmaceutical compositions for preventing and/or treating NAFLD will be described in detail.

I. Methods for Preventing and/or Treating NAFLD

Methods for preventing and/or treating NAFLD in a subject in need thereof are disclosed. In embodiments, a method for preventing NAFLD in a subject in need thereof is disclosed. Such method may include administering a composition including a therapeutically effective amount of phenylmethimazole, methimazole derivatives, and/or tautomeric cyclic thiones, or pharmaceutically-acceptable salts or solvates thereof, to the subject, wherein administration of the phenylmethimazole, methimazole derivatives, and/or tautomeric cyclic thiones is effective to prevent NAFLD. The phenylmethimazole, methimazole derivatives, and tautomeric cyclic thiones referenced herein are as previously described. In particular embodiments, the method includes administering a composition including a therapeutically effective amount of methimazole derivatives having a formula selected from (I), (II), and (III) to the subject. In further embodiments, administration of the therapeutically effective amount of phenylmethimazole, methimazole derivatives, and/or tautomeric cyclic thiones to the subject is effective to prevent NAFLD by preventing excessive accumulation of fat in a liver cell, in liver tissue, and/or in the liver of the subject. In particular embodiments, the method includes administering a composition including a therapeutically effective amount of phenylmethimazole to the subject.

Excessive accumulation of fat may be determined via standard diagnostic testing techniques for NAFLD, as previously described. For example, fat content in the liver cell, liver tissue and/or the liver may be assessed via blood tests (e.g., liver function tests including tests of liver enzymes and/or triglyceride quantification); imaging procedures (e.g., ultrasound, computerized tomography scan and/or magnetic resonance imaging); and/or liver tissue testing (e.g., liver biopsy). More specifically, excessive accumulation of fat in the liver cell, liver tissue, and/or the liver may be determined via comparison to the fat content of a normal liver cell, liver tissue, and/or the liver of a subject who is not in need of treatment for NAFLD (or to the normal level). Additionally, by way of example, the subject in need thereof may be a subject at risk for developing NAFLD and/or a subject exhibiting symptoms associated with NAFLD.

In one or more particular embodiments, a method for reducing the risk of developing NAFLD in a subject in need thereof is disclosed. In such embodiments, the method includes administering a composition including a therapeutically effective amount of phenylmethimazole, methimazole derivatives, and/or tautomeric cyclic thiones, or pharmaceutically-acceptable salts or solvates thereof, to the subject, wherein administration of the phenylmethimazole, methimazole derivatives, and/or tautomeric cyclic thiones is effective to reduce the risk of developing NAFLD in the subject. The phenylmethimazole, methimazole derivatives, and tautomeric cyclic thiones referenced herein are as previously described. In embodiments, the method includes administering a composition including a therapeutically effective amount of methimazole derivatives having a formula selected from (I), (II), and (III) to the subject. In particular embodiments, the method includes administering a composition including a therapeutically effective amount of phenylmethimazole to the subject. In further embodiments, administration of the therapeutically effective amount of phenylmethimazole, methimazole derivatives, and/or tautomeric cyclic thiones to the subject is effective to reduce the risk of developing NAFLD in the subject by preventing excessive accumulation of fat in a liver cell, in liver tissue, and/or in the liver of the subject. Excessive accumulation of fat in the liver cell, liver tissue and/or the liver may be determined via blood tests; imaging procedures, and liver tissue testing, as previously described. Additionally, by way of example, the subject in need thereof may be a subject at risk for developing NAFLD and/or a subject exhibiting symptoms associated with NAFLD.

In other embodiments, a method for treating NAFLD in a subject in need thereof is disclosed. In such embodiments, the method includes administering a composition including a therapeutically effective amount of phenylmethimazole, methimazole derivatives, and/or tautomeric cyclic thiones, or pharmaceutically-acceptable salts or solvates thereof, to the subject, wherein administration of the phenylmethimazole, methimazole derivatives, and/or tautomeric cyclic thiones is effective to treat NAFLD. The phenylmethimazole, methimazole derivatives, and tautomeric cyclic thiones referenced herein are as previously described. In embodiments, the method includes administering a composition including a therapeutically effective amount of methimazole derivatives having a formula selected from (I), (II), and (III) to the subject. In one or more particular embodiments, the method includes administering a composition including a therapeutically effective amount of phenylmethimazole to the subject. In further embodiments, administration of the therapeutically effective amount of phenylmethimazole, methimazole derivatives, and/or tautomeric cyclic thiones to the subject is effective to treat NAFLD by reducing fat content in a liver cell, in liver tissue, and/or in the liver of the subject relative to a baseline level. In still further embodiments, administration of the therapeutically effective amount of phenylmethimazole, methimazole derivatives, and/or tautomeric cyclic thiones to the subject is effective to treat NAFLD by reducing fat content in a liver cell, in liver tissue, and/or in the liver of the subject to a normal level. A reduction of fat content in a liver cell, liver tissue, and/or the liver may be determined via standard diagnostic testing techniques for NAFLD, as previously described. More specifically, a reduction of fat content may be determined via comparison, such as, e.g., visual and/or quantifiable, to the baseline level.

In other embodiments, the method includes administering a composition including a therapeutically effective amount of phenylmethimazole, methimazole derivatives, and/or tautomeric cyclic thiones to the subject, wherein administration of the phenylmethimazole, methimazole derivatives, and/or tautomeric cyclic thiones is effective to inhibit progression of NAFLD. For example, administration of a composition including the phenylmethimazole, methimazole derivatives, and/or tautomeric cyclic thiones to the subject may be effective to inhibit the progression of NAFLD: (1) from steatosis to NASH, fibrosis, and/or cirrhosis; (2) from NASH to fibrosis and/or cirrhosis; and/or (3) from fibrosis to cirrhosis. Fat content in the liver cell, liver tissue, and/or the liver and/or progression of NAFLD may be determined via blood tests; imaging procedures, and liver tissue testing. Additionally, by way of example, the subject in need thereof may be a subject exhibiting symptoms associated with NAFLD and/or a subject having NAFLD.

In one or more embodiments, the methods for preventing and/or treating NAFLD include administration of a composition including a therapeutically effective amount of phenylmethimazole, methimazole derivatives, and/or tautomeric cyclic thiones to a subject in need thereof, wherein the subject is a mammal. In one or more particular embodiments, the subject is a mammal selected from the group consisting of humans, non-human primates, canines, felines, murines, bovines, equines, porcines, and lagomorphs. In further embodiments, the subject is a human or a mouse.

In other embodiments, the methods for preventing and/or treating NAFLD include systemic administration of the phenylmethimazole, methimazole derivatives, and/or tautomeric cyclic thiones. The systemic administration of the phenylmethimazole, methimazole derivatives, and/or tautomeric cyclic thiones may be selected from the group consisting of oral, sublingual, subcutaneous, intravenous, intramuscular, intranasal, intrathecal, intraperitoneal, percutaneous, intranasal, and enteral administration, and combinations thereof. In one or more particular embodiments, the systemic administration of phenylmethimazole, methimazole derivatives, and/or tautomeric cyclic thiones is oral.

In other embodiments, the methods for preventing and/or treating NAFLD include administration of phenylmethimazole, methimazole derivatives, and/or tautomeric cyclic thiones to a subject in need thereof in a dose of from about 1 mg/kg to about 10 mg/kg, or from about 3 mg/kg to about 10 mg/kg, or from about 5 mg/kg to about 10 mg/kg. It is contemplated that such doses serve as non-limiting examples of suitable doses of phenylmethimazole, methimazole derivatives, and/or tautomeric cyclic thiones for a subject in need thereof. In one or more particular embodiments, phenylmethimazole, methimazole derivatives, and/or tautomeric cyclic thiones is administered to a subject in need thereof in a dose of about 1 mg/kg. In further embodiments, the dose of phenylmethimazole, methimazole derivatives, and/or tautomeric cyclic thiones is administered daily. In still further embodiments, the dose of phenylmethimazole, methimazole derivatives, and/or tautomeric cyclic thiones is administered at least once a day. In yet still further embodiments, the dose of phenylmethimazole, methimazole derivatives, and/or tautomeric cyclic thiones is administered more often than one time a day; for example, the dose of phenylmethimazole, methimazole derivatives, and/or tautomeric cyclic thiones is administered at least two times a day, at least three times a day, at least four times a day, at least five times a day, and/or at least six times a day.

In yet other embodiments, the methods for preventing and/or treating NAFLD include co-administering with the effective amount of phenylmethimazole, methimazole derivatives, and/or tautomeric cyclic thiones a therapeutically effective amount of one or more compounds for the treatment of metabolic syndrome, Hepatitis C, metabolic disorder, obesity, insulin resistance, inflammatory bowel disease, small-bowel diverticulosis, and/or viral infection. In some embodiments, co-administration may include administering a composition including phenylmethimazole, methimazole derivatives, and/or tautomeric cyclic thiones prior to or subsequent to administering a separate composition including the one or more other compounds. In some embodiments, co-administration may include administering a composition including the phenylmethimazole, methimazole derivatives, and/or tautomeric cyclic thiones and the one or more other compounds. In one or more particular embodiments, the methods for preventing and/or treating NAFLD include co-administering with the phneylmethimazole, methimazole derivatives, and/or tautomeric cyclic thiones a therapeutically effective amount of metformin, thiazolidinediones, and/or HMG-Co-A inhibitors (i.e., 3-hydroxy-3-methyl-glutaryl-CoA reductase inhibitors). In other particular embodiments, administration of the additional medication is systemic, as previously described.

In other embodiments, the methods for preventing and/or treating NAFLD in a subject in need thereof further include monitoring disease development and/or progression and repeating administration of the composition including the therapeutically effective amount of phenylmethimazole, methimazole derivatives, and/or tautomeric cyclic thiones, or pharmaceutically-acceptable salts or solvates thereof, one or more times, thereby preventing and/or treating NAFLD. Development and/or progression of NAFLD can be monitored in a variety of ways known to the skilled clinician, such as described with regard to diagnosis of NAFLD. For example, development and/or progression of NAFLD may be monitored via assessment of fat content in a liver cell, liver tissue, and/or the liver one or more times. In embodiments, if the appropriate assessment indicates that NAFLD is developing, advancing, and/or has not yet responded to treatment (such as, e.g., wherein an increase in fat content in a liver cell, liver tissue, and/or the liver is determined), a clinician may administer an additional dose of phenylmethimazole, methimazole derivatives, and/or tautomeric cyclic thiones. The clinician may then reassess disease progression. Successive rounds of administering phenylmethimazole, methimazole derivatives, and/or tautomeric cyclic thiones coupled with monitoring development and/or progress of NAFLD, may be necessary in order to achieve the desired prevention and/or treatment of NAFLD.

Embodiments of the methods for preventing and/or treating NAFLD have been described in detail. Further embodiments directed to pharmaceutical compositions for prevention and/or treatment of NAFLD will now be described.

II. Pharmaceutical Compositions for Prevention and/or Treatment of NAFLD

Pharmaceutical compositions for the prevention and/or treatment of NAFLD are disclosed. In one or more embodiments, a pharmaceutical composition including a therapeutically effective amount of phenylmethimazole, methimazole derivatives, and/or tautomeric cyclic thiones, or pharmaceutically-acceptable salts or solvates thereof, as an active ingredient is disclosed. In other embodiments, a pharmaceutical composition including a therapeutically effective amount of phenylmethimazole, methimazole derivatives, and/or tautomeric cyclic thiones, or pharmaceutically-acceptable salts or solvates thereof, as an active ingredient is disclosed, wherein the phenylmethimazole, methimazole derivatives, and/or tautomeric cyclic thiones is formulated for administration to a subject for the prevention and/or treatment of NAFLD. The phenylmethimazole, methimazole derivatives, and tautomeric cyclic thiones referenced herein are as previously described. In embodiments, the pharmaceutical composition includes a therapeutically effective amount of one or more methimazole derivatives having a formula selected from (I), (II), and (III).

In other embodiments, the pharmaceutical composition for the prevention and/or treatment of NAFLD further includes an additional active ingredient. In embodiments, the pharmaceutical composition for the prevention and/or treatment of NAFLD further includes a therapeutically effective amount of an additional active ingredient. In one or more particular embodiments, the pharmaceutical composition for the prevention and/or treatment of NAFLD includes a therapeutically effective amount of an additional active agent for the treatment of conditions associated with NAFLD. For example, the pharmaceutical composition for the prevention and/or treatment of NAFLD may further include an additional active agent for the treatment of metabolic syndrome, Hepatitis C, metabolic disorder, obesity, insulin resistance, inflammatory bowel disease, small-bowel diverticulosis, and/or viral infection. In particular embodiments, the pharmaceutical composition for the treatment of NAFLD includes additional active agents of metformin, thiazolidinediones, and/or HMG-Co-A inhibitors.

In some embodiments, the pharmaceutical composition for the prevention and/or treatment of NAFLD further includes a pharmaceutically acceptable carrier and/or excipient. Suitable pharmaceutically acceptable carriers may include a wide range of known diluents (i.e., solvents), fillers, extending agents, adjuvants, binders, suspending agents, disintegrates, surfactants, lubricants, wetting agents, preservatives, stabilizers, antioxidants, antimicrobials, buffering agents and the like commonly used in this field. Such carriers may be used singly or in combination according to the form of the pharmaceutical preparation. In further embodiments, a preparation resulting from the inclusion of a pharmaceutically acceptable carrier may incorporate, if necessary, one or more solubilizing agents, buffers, preservatives, colorants, perfumes, flavorings and the like, as widely used in the field of pharmaceutical preparation.

Examples of suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, and vegetable oils. A full discussion of pharmaceutically acceptable excipients is provided in Remington's Pharmaceutical Sciences I (Mack Pub. Co.), the contents of which are incorporated by reference herein. Examples of suitable adjuvants include inorganic compounds (e.g., aluminum hydroxide, aluminum phosphate, calcium phosphate hydroxide, and beryllium), mineral oil (e.g., paraffin oil), bacterial products (e g, killed bacteria Bordetelle pertussis, Mycobacterium bovis, and toxoids), nonbacterial organics (e.g., squalene and thimerosal), delivery systems (e.g., detergents (Quil A)), cytokines (e.g., IL-1, IL-2, and IL-12), and combinations (e.g., Freund's complete adjuvant, Freund's incomplete adjuvant). Examples of suitable preservatives, stabilizers, antioxidants, antimicrobials, and buffering agents include BHA, BHT, citric acid, ascorbic acid, tetracycline, and the like. Cream or ointment bases useful in formulation include lanolin, Silvadene® (Marion), Aquaphor® (Duke Laboratories).

In embodiments, the pharmaceutical composition for the prevention and/or treatment of NAFLD includes phenylmethimazole, methimazole derivatives, and/or tautomeric cyclic thiones formulated into a dosage form. In one or more particular embodiments, phenylmethimazole, methimazole derivatives, and/or tautomeric cyclic thiones is formulated into a dosage form selected from the group consisting of creams, emulsions, ointments, gels, tablets, capsules, granules, pills, injections, solutions, suspensions, and syrups. The form and administration route for such pharmaceutical composition are not limited and can be suitably selected. For example, tablets, capsules, granules, pills, syrups, solutions, emulsions, and suspensions may be administered orally. Additionally, injections (e.g., subcutaneous, intravenous, intramuscular, and intraperitoneal) may be administered intravenously either singly or in combination with a conventional replenisher containing glucose, amino acid and/or the like, or may be singly administered intramuscularly, intracutaneously, subcutaneously and/or intraperitoneally.

A pharmaceutical composition for the prevention and/or treatment of NAFLD may be prepared according to methods known in the pharmaceutical field using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

Injections, solutions, emulsions, suspensions, syrups and the like may be prepared according to known methods suitably using solvents for dissolving the active ingredient, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

In some embodiments, the pharmaceutical composition for the prevention and/or treatment of NAFLD includes a packaging material suitable for the pharmaceutical composition and instructions for use of the pharmaceutical composition for the prevention and/or treatment of NAFLD. In particular embodiments, the pharmaceutical composition for the prevention and/or treatment of NAFLD is provided for administration to a subject in unit dose and/or multi-dose containers, e.g., vials and/or ampoules. In specific embodiments, the pharmaceutical composition for the prevention and/or treatment of NAFLD is provided for administration to a subject in a device including a reservoir. In further specific embodiments, the pharmaceutical composition for the prevention and/or treatment of NAFLD is provided for administration to a subject in a device including a reservoir which is a vial, wherein the device is a syringe.

The pharmaceutical compositions for the prevention and/or treatment of NAFLD as described herein may be administered to a subject in need thereof in accordance with the methods for preventing and/or treating NAFLD, as described in an earlier section.

In some embodiments, phenylmethimazole, methimazole derivatives, and/or tautomeric cyclic thiones for use in the prevention and/or treatment of NAFLD is/are disclosed. In other embodiments, phenylmethimazole, methimazole derivatives, and/or tautomeric cyclic thiones for use in reducing the risk of acquiring NAFLD is/are disclosed. The phenylmethimazole, methimazole derivatives, and tautomeric cyclic thiones referenced herein are as previously described. In embodiments, the phenylmethimazole, methimazole derivatives, and/or tautomeric cyclic thiones further include an additional active ingredient for the treatment of conditions associated with NAFLD, as previously described. In other embodiments, the phenylmethimazole, methimazole derivatives, and/or tautomeric cyclic thiones are incorporated into a pharmaceutical composition for the prevention and/or treatment of NAFLD and/or are formulated into a dosage form for the prevention and/or treatment of NAFLD, as previously described.

Embodiments of the pharmaceutical compositions for the prevention and/or treatment of NAFLD have been described in detail.

It should now be understood that various aspects of the present disclosure are described herein and that such aspects may be utilized in conjunction with various other aspects:

In a first aspect, a method for preventing or treating non-alcoholic fatty liver disease (NAFLD) in a subject in need thereof is disclosed. The method includes administering a composition including a therapeutically effective amount of phenylmethimazole, methimazole derivatives, and/or tautomeric cyclic thiones, or pharmaceutically acceptable salts or solvates thereof, to the subject.

In a second aspect, a method according to the first aspect is disclosed, wherein administration of the phenylmethimazole, methimazole derivatives, and/or tautomeric cyclic thiones is effective to prevent NAFLD.

In a third aspect, a method according to any of the first or the second aspects is disclosed, wherein administration of the phenylmethimazole, methimazole derivatives, and/or tautomeric cyclic thiones is effective to prevent NAFLD by preventing excessive accumulation of fat in liver tissue of the subject.

In a fourth aspect, a method according to any of the first to the third aspects is disclosed, wherein administration of the phenylmethimazole, methimazole derivatives, and/or tautomeric cyclic thiones is effective to prevent NAFLD by preventing excessive accumulation of fat in liver tissue of the subject and the excessive accumulation of fat in the liver tissue is >55 mg fat/g of the liver tissue.

In a fifth aspect, a method according to the first aspect is disclosed, wherein administration of the phenylmethimazole, methimazole derivatives, and/or tautomeric cyclic thiones is effective to treat NAFLD.

In a sixth aspect, a method according to the first or the fifth aspects is disclosed, wherein administration of the phenylmethimazole, methimazole derivatives, and/or tautomeric cyclic thiones is effective to treat NAFLD by reducing fat content in liver tissue of the subject relative to a baseline level.

In a seventh aspect, a method according to any of the first to the sixth aspects is disclosed, wherein the subject is a mammal.

In an eighth aspect, a method according to any of the first to the seventh aspects is disclosed, wherein the subject is a mouse or a human.

In a ninth aspect, a method according to any of the first to the eighth aspects is disclosed, wherein the phenylmethimazole, methimazole derivatives, and/or tautomeric cyclic thiones is administered systemically.

In a tenth aspect, a method according to any of the first to the ninth aspects is disclosed, wherein the phenylmethimazole, methimazole derivatives, and/or tautomeric cyclic thiones is administered in a dose of from about 1 mg/kg to about 10 mg/kg.

In an eleventh aspect, a method according to any of the first to the tenth aspects is disclosed, wherein the phenylmethimazole, methimazole derivatives, and/or tautomeric cyclic thiones is administered in a dose of from about 3 mg/kg to about 10 mg/kg.

In a twelfth aspect, a method according to any of the first to the eleventh aspects is disclosed, wherein the phenylmethimazole, methimazole derivatives, and/or tautomeric cyclic thiones is administered in a dose of from about 5 mg/kg to about 10 mg/kg.

In a thirteenth aspect, a method according to any of the first to the tenth aspects is disclosed, wherein the phenylmethimazole, methimazole derivatives, and/or tautomeric cyclic thiones is administered in a dose of from about 1 mg/kg to about 10 mg/kg daily.

In a fourteenth aspect, a method according to any of the first to the eleventh aspects is disclosed, wherein the phenylmethimazole, methimazole derivatives, and/or tautomeric cyclic thiones is administered in a dose of from about 3 mg/kg to about 10 mg/kg once daily.

In a fifteenth aspect, a method according to any of the first to the fourteenth aspects is disclosed, further including co-administering at least one of metformin, a thiazolidinedione, or an HMG-Co-A inhibitor.

In a sixteenth aspect, a method for reducing the risk of developing non-alcoholic fatty liver disease (NAFLD) in a subject in need thereof is disclosed, the method including administering a composition including a therapeutically effective amount of phenylmethimazole, methimazole derivatives, and/or tautomeric cyclic thiones, or pharmaceutically acceptable salts or solvates thereof, to the subject.

In a seventeenth aspect, a pharmaceutical composition for prevention or treatment of non-alcoholic fatty liver disease (NAFLD) is disclosed, the pharmaceutical composition including phenylmethimazole, methimazole derivatives, and/or tautomeric cyclic thiones, or pharmaceutically acceptable salts or solvates thereof, formulated for administration to a subject for the prevention or treatment of NAFLD.

In an eighteenth aspect, a pharmaceutical composition according to the seventeenth aspect is disclosed, further including a pharmaceutically acceptable carrier.

In a nineteenth aspect, a device including a reservoir of the pharmaceutical composition according to any of the seventeenth to the eighteenth aspects is disclosed.

In a twentieth aspect, a device according to the nineteenth aspect is disclosed, wherein the reservoir is a vial and the device is a syringe.

In a twenty-first aspect, a method for prevention or treatment of non-alcoholic fatty liver disease (NAFLD) is disclosed; the method including administering a composition including a therapeutically effective amount of the pharmaceutical composition according to any of the seventeenth to the eighteenth aspects to the subject is disclosed.

In a twenty-second aspect, a method according to the twenty-first aspect is disclosed, wherein the pharmaceutical composition further includes a pharmaceutically acceptable carrier.

In a twenty-third aspect, a method according to the twenty-first or the twenty-second aspect is disclosed, wherein the phenylmethimazole, methimazole derivatives, and/or tautomeric cyclic thiones is formulated into a dosage form selected from the group consisting of tablets, capsules, granules, pills, injections, solutions, emulsions, suspensions, and syrups.

In a twenty-fourth aspect, a pharmaceutical composition according to the seventeenth or eighteenth aspects is disclosed, the pharmaceutical composition further including an additional active agent for the treatment of conditions associated with NAFLD.

In a twenty-fifth aspect, a pharmaceutical composition according to the seventeenth, eighteenth, or twenty-fourth aspects is disclosed, the pharmaceutical composition further including an additional active agent for the treatment of metabolic syndrome, Hepatitis C, metabolic disorder, obesity, insulin resistance, inflammatory bowel disease, small-bowel diverticulosis, and/or viral infection.

In a twenty-sixth aspect, a pharmaceutical composition according to the seventeenth, eighteenth, twenty-fourth, or twenty-fifth aspects is disclosed, the pharmaceutical composition further including an additional active ingredient in therapeutics such as metformin, thiazolidinediones, or HMG-Co-A inhibitors.

In a twenty-seventh aspect, a method for preventing or treating non-alcoholic fatty liver disease (NAFLD) in a subject in need thereof is disclosed, the method including administering a composition including a therapeutically effective amount of one or more methimazole derivatives to the subject, the methimazole derivatives having a formula selected from (I), (II), and (III).

In a twenty-eighth aspect, a method according to the twenty-seventh aspect is disclosed, wherein administration of the one or more methimazole derivatives is effective to prevent NAFLD.

In a twenty-ninth aspect, a method according to the twenty-sixth or the twenty-seventh aspects is disclosed, wherein administration of the one or more methimazole derivatives is effective to prevent NAFLD by preventing excessive accumulation of fat in liver tissue of the subject.

In a thirtieth aspect, a method according to the twenty-sixth to the twenty-ninth aspects is disclosed, wherein administration of the one or more methimazole derivatives is effective to prevent NAFLD by preventing accumulation of fat in liver tissue of the subject above a normal level.

In a thirty-first aspect, a method according to the twenty-sixth aspect is disclosed, wherein administration of the composition is effective to treat NAFLD.

In a thirty-second aspect, a method according to the twenty-sixth or the thirty-first aspect is disclosed, wherein administration of the composition is effective to treat NAFLD by reducing fat content in liver tissue of the subject relative to a baseline level.

In a thirty-third aspect, a method according to the twenty-sixth to the thirty-second aspects is disclosed, wherein the composition includes a methimazole derivative according to Formula (I), and wherein $R^3$ is selected from $C_1$-$C_4$ alkyl, $C_1$-$C_4$ substituted alkyl, and —$CH_2Ph$.

In a thirty-fourth aspect, a method according to the twenty-sixth to the thirty-third aspects is disclosed, wherein the composition includes a methimazole derivative according to Formula (I), and wherein one Y has the phenyl moiety of Formula (IV).

In a thirty-fifth aspect, a method according to the twenty-sixth to the thirty-fourth aspects is disclosed, wherein the composition includes a methimazole derivative according to Formula (I), and wherein at least one Y is $NO_2$ when Z is $C_1$-$C_4$ alkyl.

In a thirty-sixth aspect, a method according to the twenty-sixth to the thirty-third aspects is disclosed, wherein the composition includes a methimazole derivative according to Formula (I), and wherein $R^2$ and $R^3$ are independently selected from $C_1$-$C_4$ alkyl when Y is not the phenyl moiety of Formula (IV).

In a thirty-seventh aspect, a method according to the twenty-sixth to the thirty-second aspects is disclosed, wherein the composition includes phenylmethimazole according to Formula (I).

In a thirty-eighth aspect, a method according to the thirty-seventh aspect is disclosed, wherein administration of the phenylmethimazole is effective to prevent NAFLD.

In a thirty-ninth aspect, a method according to the thirty-seventh aspect is disclosed, wherein administration of the phenylmethimazole is effective to treat NAFLD.

In a fortieth aspect, a method according to the thirty-seventh to the thirty-ninth aspects is disclosed, wherein the phenylmethimazole is administered in a dose of from about 1 mg/kg to about 10 mg/kg.

In a forty-first aspect, a method according to the thirty-seventh to the fortieth aspects is disclosed, wherein the phenylmethimazole is administered in a dose of from about 5 mg/kg to about 10 mg/kg.

In a forty-second aspect, a method according to the thirty-seventh to the forty-first aspects is disclosed, wherein the phenylmethimazole is administered in a dose of from about 1 mg/kg to about 10 mg/kg daily.

In a forty-third aspect, a method according to the thirty-seventh to the forty-second aspects is disclosed, wherein the phenylmethimazole is administered in a dose of from about 3 mg/kg to about 10 mg/kg once daily.

In a forty-fourth aspect, a method according to the twenty-sixth to the thirty-second aspects is disclosed, wherein the composition includes a methimazole derivative according to Formula (II), and wherein X is S.

In a forty-fifth aspect, a method according to the twenty-sixth to the thirty-second aspects is disclosed, wherein the composition includes a methimazole derivative according to Formula (III), and wherein X is S.

In a forty-sixth aspect, a method according to the twenty-sixth to the forty-fifth aspects is disclosed, wherein administration of the subject is a mammal.

In a forty-seventh aspect, a method according to the twenty-sixth to the forty-sixth aspects is disclosed, wherein the subject is a mouse or a human.

In a forty-eighth aspect, a method according to the twenty-sixth to the forty-seventh aspects is disclosed, wherein the one or more methimazole derivatives is administered systemically.

In a forty-ninth aspect, a method according to the twenty-sixth to the forty-eight aspects is disclosed, further including co-administering at least one of metformin, a thiazolidinedione, or an HMG-Co-A inhibitor.

In a fiftieth aspect, a method for preventing or treating non-alcoholic fatty liver disease (NAFLD) in a subject in need thereof is disclosed, the method including administering a composition including a therapeutically effective amount of one or more methimazole derivatives to the subject, wherein the one or more methimazole derivatives have a formula selected from (X) and (XI).

In a fifty-first aspect, a method according to the fiftieth aspect is disclosed, wherein the composition includes one or more methimazole derivatives having Formulae (XII) or (XIII) according to Formula (X), wherein $R^9$ is selected from —OH, -M, and —OOCCH$_2$M; and wherein M is a halogen.

In a fifty-second aspect, a method according to the fifty-first aspect is disclosed, wherein the composition includes one or more of methimazole derivatives having Formula (XIV) according to Formula (XI), wherein $R^9$ is selected from —OH, -M, and —OOCCH$_2$M; and wherein M is a halogen.

In a fifty-third aspect, a method for reducing the risk of developing non-alcoholic fatty liver disease (NAFLD) in a subject in need thereof is disclosed, the method including administering a composition including a therapeutically effective amount of phenylmethimazole, or a pharmaceutically-acceptable salt or solvate thereof, to the subject.

In a fifty-fourth aspect, a pharmaceutical composition for prevention or treatment of non-alcoholic fatty liver disease (NAFLD) is disclosed, the pharmaceutical composition including: (a) a therapeutically effective amount of one or more of metformin, thiazolidinediones, or HMG-Co-A inhibitors; and (b) a therapeutically effective amount of one or more methimazole derivatives having a formula selected from (I), (II), and (III), or pharmaceutically-acceptable salts or solvates thereof.

In a fifty-fifth aspect, a pharmaceutical composition according to the fifty-fourth aspect is disclosed, the pharmaceutical composition further including a pharmaceutically acceptable carrier.

In a fifty-sixth aspect, a device including a reservoir of the pharmaceutical composition according to the fifty-fourth to the fifty-fifth aspects is disclosed.

In a fifty-seventh aspect, a method for prevention or treatment of non-alcoholic fatty liver disease (NAFLD) is disclosed, the method including administering a therapeutically effective amount of the pharmaceutical composition according to the seventeenth or the eighteenth aspect or according to the fifty-fourth to the fifty-sixth aspect.

EXAMPLES

The following non-limiting examples illustrate the methods of the present disclosure.

Example 1

Evaluation of Onset of NAFLD in C57BL/6J Mice Fed High Fat Diet

Experimental Protocol. C57BL/6J mice (i.e., a mouse model of obesity-induced insulin resistance and Type 2 Diabetes Mellitus) were placed on a high-fat diet (hereinafter, "HFD") containing 60% fat (by % Kcal) (Diet #D12492, Research Diets, Inc., New Brunswick, N.J.) for 8 weeks. 3 of such mice were euthanized each week during this 8-week period for evaluation of NAFLD. Mice fed a low fat diet (hereinafter, "LFD") containing 10% fat (by % Kcal) (Diet #D12450B, Research Diets) served as a control. More particularly, two mice fed the LFD served as a control (and were euthanized) for each week that the mice fed the HFD were euthanized over the 8 week period. The following Table further illustrates the experimental design:

TABLE II

Onset of NAFLD Experimental Protocol

| Time (Weeks) | Total Number of Mice | Number of Mice Euthanized for Fatty Liver Evaluation |
|---|---|---|
| 0 | 85 | 5 (3 HFD + 2 LFD mice) |
| 1 | 80 | 5 (3 HFD + 2 LFD mice) |
| 2 | 75 | 5 (3 HFD + 2 LFD mice) |
| 3 | 70 | 5 (3 HFD + 2 LFD mice) |
| 4 | 65 | 5 (3 HFD + 2 LFD mice) |
| 5 | 60 | 5 (3 HFD + 2 LFD mice) |
| 6 | 55 | 5 (3 HFD + 2 LFD mice) |
| 7 | 50 | 5 (3 HFD + 2 LFD mice) |
| 8 | 45 | 5 (3 HFD + 2 LFD mice) |

As previously described, NAFLD may be detected macroscopically (i.e., via the naked eye), microscopically (i.e., via tissue sections of the liver, e.g., imaging procedures and/or liver biopsy), and/or molecularly (i.e., using molecular assays to quantify liver triglycerides, e.g., blood testing). NAFLD was evaluated in the liver of the HFD and LFD mice macroscopically, microscopically, and molecularly. More specifically, following euthanasia, the liver of each mouse was removed, weighed, and photographs taken thereof for macroscopic and/or gross observation of NAFLD. Then, the liver of each mouse was split in half, wherein one half was used for microscopic analysis of NAFLD and the remaining half was used for molecular analysis of NAFLD (i.e., quantification of triglycerides).

Triglycerides were quantified in accordance with the following general protocol, based upon the Salmon and Flatt Method of Liver Saponification. 50-100 mg of liver tissue was placed into an Eppendorf tube and weighed. Equal volume per weight of 3 M KOH (in 65% EtOH) was added to the tube and vortexed. The tube was placed at 70° C. for 1 hr to activate digestion. The tubes were vortexed every 15 minutes. The tube was set at room temperature overnight to allow for complete digestion, and was vortexed periodically. The sample was diluted to a final concentration of 100 mg of liver tissue per 600 μl fluid; the sample was diluted by adding 2 M Tris-HCl (un-pHed) to a final concentration of 50 mM. Where a second dilution was required, the sample was diluted using 50 mM Tris-HCl (pH 7.5). Triglycerides- GPO (0.5 mL, liquid; Pointe Scientific Cat. No. T7532-500; Fisher Scientific, Pittsburgh, Pa.) were aliquoted into Eppendorf tubes and warmed in a 37° C. water bath for 5-10 minutes. Glycerol standards (0, 1, 2.5, 5, 7.5 and 10 mmol/L) were made by diluting 10 mmol/L stock of glycerol, such as, e.g., with 50 mM Tris-HCl. 5 µL of the sample and glycerol standards (0, 1, 2.5, 5, 7.5 and 10 mmol/L) were added to 0.5 mL of the triglycerides-GPO, mixed, and incubated at room temperature for 5 minutes. The mixture was then vortexed and added (200 µL) to each well of a 96-well flat-bottom ELISA plate (in duplicate). Absorbance (i.e., optical density) was read at 500 nm. The concentrations of the samples were determined via use of a plot of glycerol standards concentration (mmol/L) with respect to optical density (i.e., O.D.) at 500 nm. The concentration of glycerol (mg glycerol/g tissue) was then calculated and triglyceride concentration was determined, in accordance with calculations known to those of ordinary skill in the art.

The experimental protocol described above was conducted in duplicate.

Figure 2:
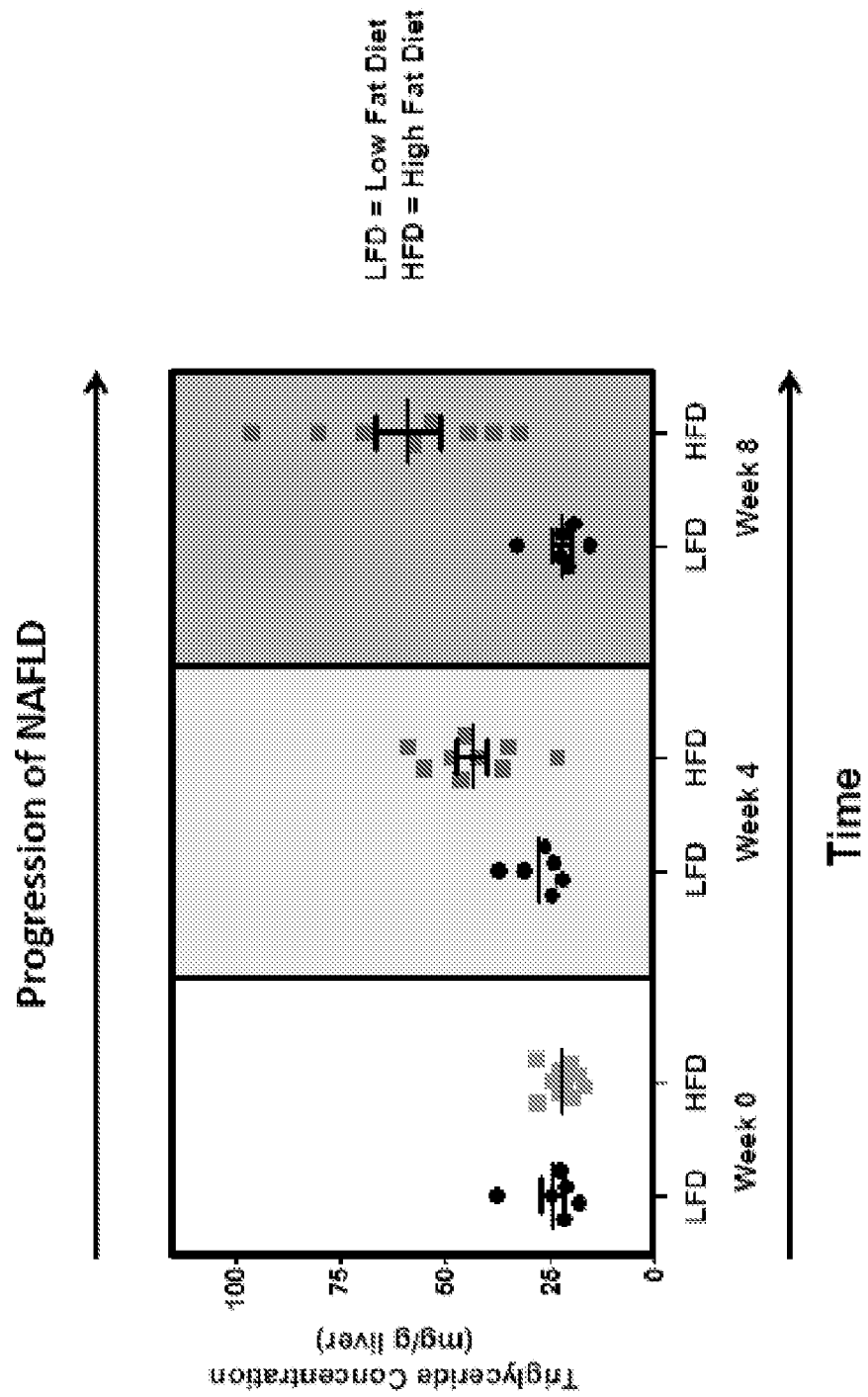
FIG. 2 is a graph of C57BL/6J mice on a low fat diet (i.e., LFD) and C57BL/6J mice on a high fat diet (i.e., HFD) at 0 weeks, 4 weeks, and 8 weeks with respect to triglyceride concentration (mg/g liver)

Experimental Results. As shown in FIGS. 1-2, the onset and/or development of NAFLD in C57BL/6J mice was characterized microscopically and molecularly. More specifically, upon removal of the liver tissue from the C57BL/6J mice, it was macroscopically and microscopically observed that the liver tissue from the C57BL/6J mice fed the HFD had greater fat content at weeks 4 and 8 in comparison to the liver tissue from the C57BL/6J fed the LFD (see e.g., FIG. 1). Moreover, as shown in FIG. 1, progression of NAFLD was microscopically observed in C57BL/6J mice fed a HFD from weeks 0-8, wherein excessive accumulation of fat was evident in C57BL/6J mice fed a HFD at week 4, and was clearly observed in C57BL/6J mice fed a HFD at week 8.

Such macroscopic and microscopic observations were confirmed molecularly. FIG. 2 includes triglyceride content of C57BL/6J mice from both characterization studies (i.e., from the experimental protocol described above conducted in duplicate). More particularly, FIG. 2 includes triglyceride content of 6 C57BL/6J mice fed a HFD for each of weeks 0, 4, and 8 and 4 C57BL/6J mice fed a LFD for each of weeks 0, 4, and 8. As shown in FIG. 2, the liver tissue from the C57BL/6J mice fed the HFD had a greater triglyceride content (mg/g liver) at weeks 4 and 8 in comparison to the liver tissue from the C57BL/6J fed the LFD. Moreover, as shown in FIG. 2, the triglyceride content of the liver tissue from the C57BL/6J mice fed the HFD increased from weeks 0-8. Thus, without being bound by the theory, it is believed that NAFLD develops in C57BL/6J mice fed the HFD by at least week 4.

Example 2

Evaluation of Phenylmethimazole in Preventing NAFLD in Mice

Experimental Protocol. 7 week old male C57BL/6J mice were placed on either a LFD (i.e., having a fat content of 10%, N=8) or a HFD (i.e., having a fat content of 60%, N=40). The mice placed on the LFD served as a control. The C57BL/6J mice on the HFD were immediately given an intraperitoneal sham injection (N=8), an intraperitoneal injection of dimethyl sulfoxide (hereinafter, "DMSO", N=8), an intraperitoneal injection of 0.1 mg/kg phenylmethimazole (N=8), an intraperitoneal injection of 1 mg/kg phenylmethimazole (N=8), or an intraperitoneal injection of 10 mg/kg phenylmethimazole (N=8). Such injections were given to the C57BL/6J mice on the HFD once daily for a period of 18 weeks.

After 18 weeks, all of the C57BL/6J mice were euthanized. Liver tissue of the euthanized C57BL/6J mice was harvested and micrograph analysis was performed. More specifically, NAFLD was evaluated in the liver tissue of the euthanized C57BL/6J mice microscopically and molecularly. Following euthanasia, the liver of each mouse was removed and divided, wherein one portion was used for the microscopic analysis of NAFLD and another portion was used for the molecular analysis of NAFLD (i.e., quantification of triglycerides). Quantification of triglycerides was performed in accordance with the general protocol described in Example 1.

Figure 3:
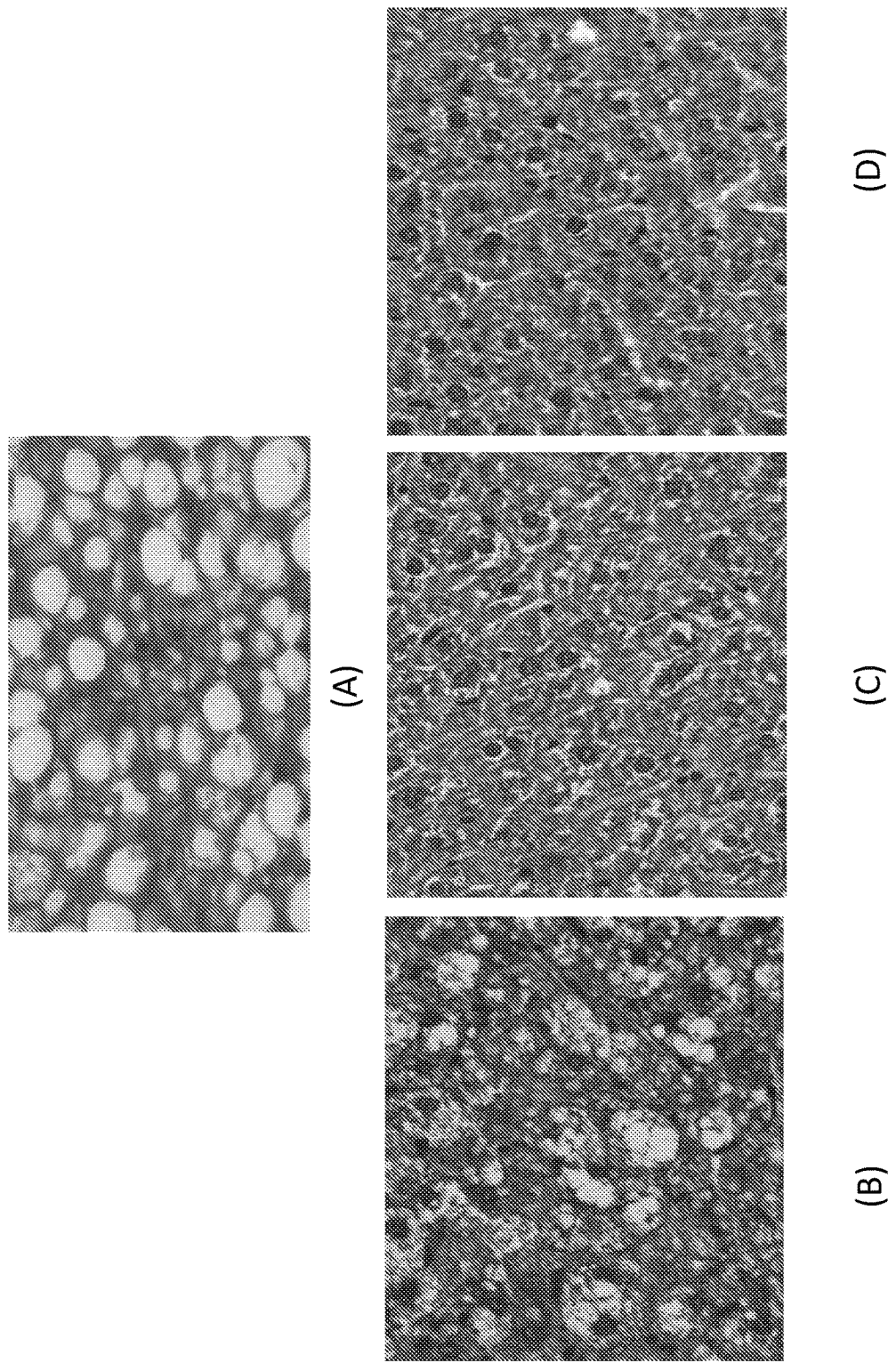
FIG. 3 is a micrograph of liver tissue harvested from C57BL/6J mice on a high fat diet (N=40), wherein the C57BL/6J mice were administered (A) dimethyl sulfoxide (N=8); (B) 0.1 mg/kg phenylmethimazole (N=8); (C) 1 mg/kg phenylmethimazole (N=8); or (D) 10 mg/kg phenylmethimazole (N=8) once daily for 18 weeks.

Experimental Results. Upon removal of the liver tissue from the C57BL/6J mice, it was macroscopically observed that the liver tissue from the mice fed a HFD injected with phenylmethimazole (0.1 mg/kg, 1 mg/kg, or 10 mg/kg) had much less fatty liver disease despite obesity when compared to the mice fed a HFD which received a sham injection or were injected with DMSO, despite being obese and diabetic. Such macroscopic observations were confirmed microscopically. As shown in FIG. 3(B)-(D), the mice fed the HFD which were injected with phenylmethimazole had much less fatty liver disease when compared to the mice fed the HFD which received a sham injection (data not shown) or which were injected with DMSO (as shown in FIG. 3(A)).

Figure 4:
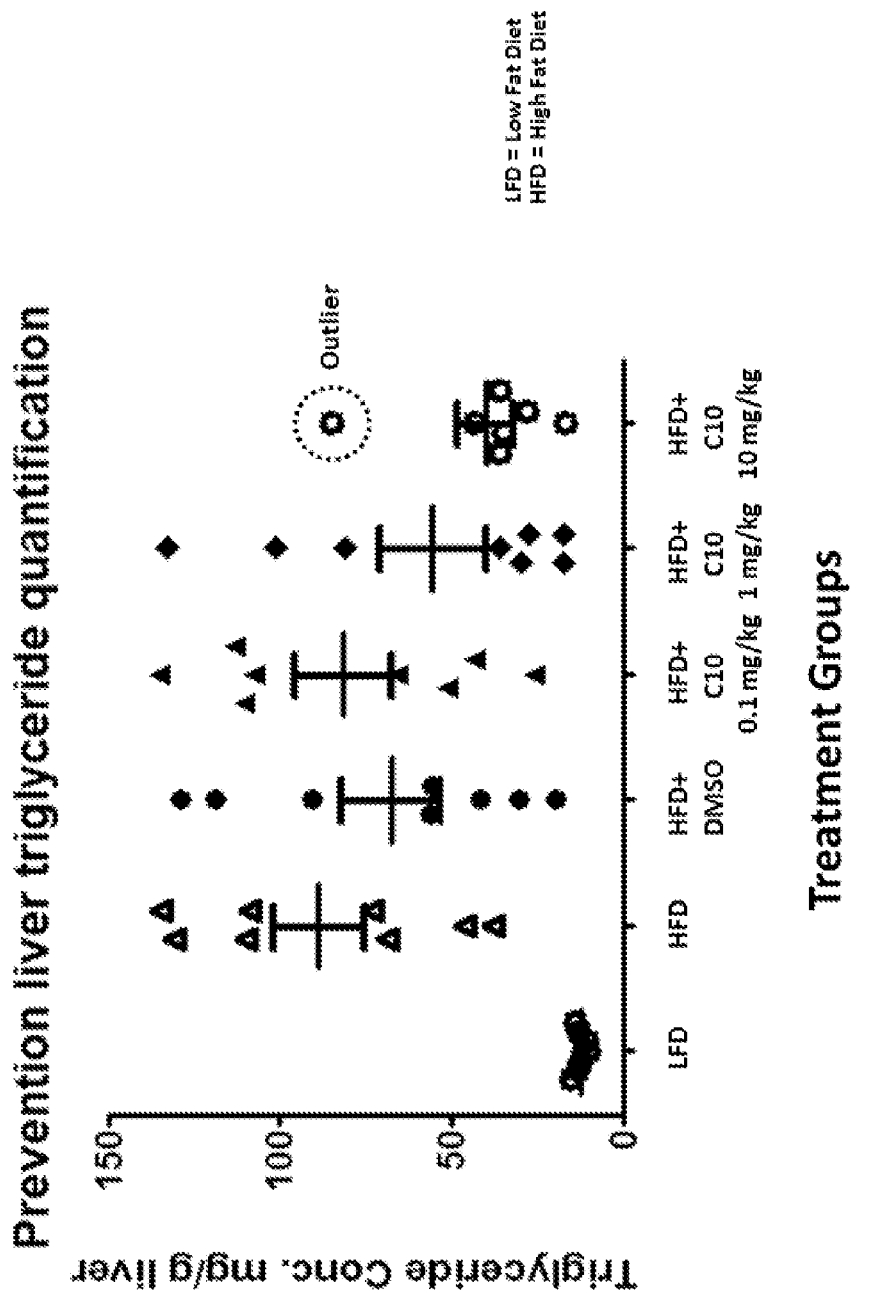
FIG. 4 is graph of C57BL/6J mice on a low fat diet (i.e., LFD) for a period of 18 weeks, C57BL/6J mice on a high fat diet (i.e., HFD) for a period of 18 weeks, and C57BL/6J mice on a HFD which were administered DMSO once daily (i.e., HFD+DMSO) or C10 once daily (i.e., HFD+C10 0.1 mg/kg, HFD+C10 1 mg/kg, or HFD+C10 10 mg/kg) for a period of 18 weeks, with respect to triglyceride concentration (mg/g liver).

Additionally, as shown in FIG. 4, such microscopic observations were confirmed molecularly. More specifically, the amount of triglyceride content (mg/g liver) was measured in the liver tissue of the mice fed the LFD, the mice fed the HFD, and the mice fed the HFD which were injected with phenylmethimazole (0.1 mg/kg, 1 mg/kg, or 10 mg/kg). As shown in FIG. 4, the liver tissue of the mice fed the HFD treated with phenylmethimazole (1 mg/kg or 10 mg/kg) exhibited a lower triglyceride concentration (mg/g liver) than mice fed the HFD wherein no phenymethimazole was administered. Without being bound by the theory, it is believed that phenymethimazole prevented NAFLD in the mice fed the HFD in a dose-dependent manner. Such results indicate that phenylmethimazole is useful in the prevention of NAFLD.

It is specifically contemplated that the conclusions made herein based upon the described observations in mice are also applicable to other mammals, including humans. Additionally, one of skill in the art will understand that the specific dosage for use in humans may vary.

Example 3

Evaluation of Phenylmethimazole in Treating NAFLD in C57BL/6J Mice Fed High Fat Diet Experimental Protocol. C57BL/6J mice are placed on an HFD containing 60% fat (by % Kcal) (Diet #D12492, Research Diets, Inc.) for a period of weeks (as determined by the results of Example 1) until development of NAFLD is observed and clearly distinguishable from LFD-fed mice of the same age (between 4-8 weeks). At the time or after NAFLD is observed, once daily ip injections of phenylmethimazole (i.e., C10), DMSO, or sham are administered. 5 mice are then euthanized weekly thereafter to characterize the effects of C10, DMSO, and/or sham on treatment of NAFLD for the period of 16 weeks post-initiation of C10, DMSO, and sham administration. The period of time for which treatment is administered will be extended to 24 weeks if no effect of C10 administration on treatment of NAFLD is observed. The following Table further illustrates the experimental design:

TABLE 3

16-Week Treatment of NAFLD Experimental Protocol

| Group | (n) | Diet | Treatment | |
|---|---|---|---|---|
| 1 | 85 | HFD | Sham | Stress Control |
| 2 | 85 | HFD | DMSO | Vehicle Control |
| 3 | 85 | HFD | C10 Low | 1 mg/kg/day |
| 4 | 85 | HFD | C10 Medium | 3 mg/kg/day |
| 5 | 85 | HFD | C10 High | 10 mg/kg/day |

If no effect of C10 administration on treatment of NAFLD is observed by 16 weeks post-initiation of C10, DMSO, and sham administration, a subsequent study is performed wherein the period of time is extended to 24 weeks of C10 administration, with 5 mice euthanized weekly from weeks 17-24 as previously described. The following Table further illustrates the experimental design:

TABLE 4

17-24-Week Treatment of NAFLD Experimental Protocol

| Group | (n) | Diet | Treatment | |
|---|---|---|---|---|
| 1 | 40 | HFD | Sham | Stress Control |
| 2 | 40 | HFD | DMSO | Vehicle Control |
| 3 | 40 | HFD | C10 Low | 1 mg/kg/day |
| 4 | 40 | HFD | C10 Medium | 3 mg/kg/day |
| 5 | 40 | HFD | C10 High | 10 mg/kg/day |

NAFLD is evaluated in the liver of the HFD mice macroscopically, microscopically, and molecularly. More specifically, following euthanasia, the liver of each mouse is removed, weighed, and photographs taken thereof for macroscopic and/or gross observation of NAFLD. Then, the liver of each mouse is split in half, wherein one half is used for microscopic analysis of NAFLD and the remaining half is used for molecular analysis of NAFLD (i.e., quantification of triglycerides). Quantification of triglycerides is performed in accordance with the general protocol described in Example 1.

Experimental Results. It is contemplated that the fat content in the liver tissue of the mice is reduced relative to a baseline level, such that the phenlymethimazole is effective to treat NAFLD. It is specifically contemplated that the conclusions made herein based upon the described observations in mice are also applicable to other mammals, including humans.

Example 4

Therapeutic Use of Phenylmethimazole to Prevent Development of NAFLD

Experimental Protocol. A patient at risk for developing NAFLD is prescribed phenylmethimazole to prevent excess accumulation of fat. The patient takes a once daily oral dose of 1 mg/kg of body weight of phenylmethimazole chronically, during which fat content in the liver is determined via liver function testing, liver ultrasound, and liver biopsy.

Experimental Results. It is contemplated that no excess accumulation of fat has occurred in the patient, such that phenylmethimazole is effective to prevent NAFLD.

Example 5

Therapeutic Use of Phenylmethimazole to Treat NAFLD

Experimental Protocol. A patient having NAFLD is prescribed phenylmethimazole to reduce the fat content in his liver. After determination of a baseline level of fat content in his liver, the patient takes a once daily oral dose of 3 mg/kg of body weight of phenylmethimazole for a period of 16 weeks, during which fat content in his liver tissue is determined via liver function testing, liver ultrasound, and liver biopsy.

Experimental Results. It is contemplated that the fat content in the patient's liver is reduced relative to the baseline level, such that the phenlymethimazole is effective to treat NAFLD.

Example 6

Pharmaceutical Compositions for Prevention and/or Treatment of NAFLD

Useful pharmaceutical formulations for administration of phenylmethimazole, methimazole derivatives, and/or tautomeric cyclic thiones may be as described below and may be made using conventional techniques:

CAPSULES

| | |
|---|---|
| Active ingredient | 0.01 to 10 mg |
| Lactose | 20-100 mg |
| Corn Starch U.S.P. | 20-100 mg |
| Aerosolized silica gel | 2-4 mg |
| Magnesium stearate | 1-2 mg |

TABLETS

| | |
|---|---|
| Active ingredient | 0.01 to 10 mg |
| Microcrystalline cellulose | 50 mg |
| Corn Starch U.S.P. | 80 mg |
| Lactose U.S.P. | 50 mg |
| Magnesium stearate U.S.P. | 1-2 mg |

This tablet can be sugar coated according to conventional art practices. Colors may be added to the coating.

CHEWABLE TABLETS

| | |
|---|---|
| Active ingredient | 0.01 to 10 mg |
| Mannitol, N.F. | 100 mg |
| Flavor | 1 mg |
| Magnesium stearate U.S.P. | 2 mg |

INJECTABLE

| | |
|---|---|
| Active ingredient | 0.05 to 60 mg |
| Polyethylene glycol 600 | 1.0 cc |
| Sodium bisulfite, U.S.P. | 0.4 mg |
| Water for injection, U.S.P. (q.s.) | 2.0 cc |

It is noted that terms like "preferably," "generally," "commonly," and "typically" are not utilized herein to limit the scope of the claims or to imply that certain features are critical, essential, or even important to the structure or function of the claims. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

All documents cited are incorporated herein by reference; the citation of any document is not to be construed as an admission that it is prior art with respect to the present disclosure.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present disclosure have been illustrated and described, it would be obvious to one skilled in the art that various other changes and modifications can be made without departing from the spirit and scope of the disclosure. It is therefore intended to cover in the appended claims all such changes and modifications that are within the scope of this disclosure.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Throughout the specification and claims, a given chemical formula or name shall encompass all tautomers and optical and stereoisomers, as well as racemic mixtures where such isomers and mixtures exist.

The invention claimed is:

1. A method for treating or reducing the risk of developing non-alcoholic fatty liver disease (NAFLD) in a subject in need thereof, the method comprising administering a composition comprising a therapeutically effective amount of one or more methimazole derivatives to the subject, the methimazole derivatives having a formula selected from (I), (II), and (III):

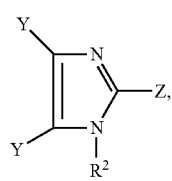

(I)

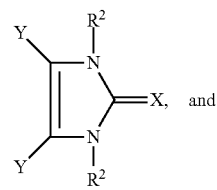

(II)

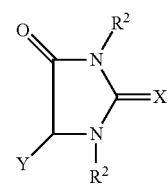

(III)

or pharmaceutically-acceptable salts or solvates thereof; wherein:
(a) Y is independently selected from H, $C_1$-$C_4$ alkyl, $C_1$-$C_4$ substituted alkyl, $NO_2$, and a phenyl moiety having Formula (IV):

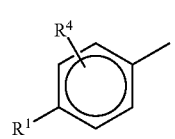

(IV)

wherein no more than one Y of a methimazole derivative may be the phenyl moiety of Formula (IV); $R^1$ is selected from H, OH, halogens, $C_1$-$C_4$ alkyl, $C_1$-$C_4$ substituted alkyl, $C_1$-$C_4$ ester, and $C_1$-$C_4$ substituted ester; and $R^4$ is selected from H, $C_1$-$C_4$ alkyl, and $C_1$-$C_4$ substituted alkyl;
(b) $R^2$ is independently selected from H, $C_1$-$C_4$ alkyl, and $C_1$-$C_4$ substituted alkyl;
(c) Z is selected from $SR^3$, $S(O)R^3$, $OR^3$, and $C_1$-$C_4$ alkyl; wherein $R^3$ is selected from H, $C_1$-$C_4$ alkyl, $C_1$-$C_4$ substituted alkyl, and —$CH_2Ph$, wherein Ph is phenyl; and
(d) X is selected from S and O.

2. The method according to claim 1, wherein administration of the one or more methimazole derivatives is effective to treat NAFLD.

3. The method according to claim 1, wherein administration of the one or more methimazole derivatives is effective to treat NAFLD by reducing fat content in liver tissue of the subject relative to a baseline level.

4. The method according to claim 1, wherein the composition comprises a methimazole derivative according to Formula (I), and wherein $R^3$ is selected from $C_1$-$C_4$ alkyl, $C_1$-$C_4$ substituted alkyl, and —$CH_2Ph$.

5. The method according to claim 1, wherein the composition comprises a methimazole derivative according to Formula (I), and wherein one Y has the phenyl moiety of Formula (IV).

6. The method according to claim 1, wherein the composition comprises a methimazole derivative according to Formula (I), and wherein at least one Y is $NO_2$ when Z is $C_1$-$C_4$ alkyl.

7. The method according to claim 1, wherein the composition comprises a methimazole derivative according to Formula (I), and wherein R² and R³ are independently selected from C₁- C₄ alkyl when Y is not the phenyl moiety of Formula (IV).

8. The method according to claim 1, wherein the composition comprises a methimazole derivative according to Formula (I), and wherein the methimazole derivative according to Formula (I) is phenylmethimazole.

9. The method according to claim 8, wherein the phenylmethimazole is administered in a dose of from about 1 mg/kg to about 10 mg/kg once daily.

10. The method according to claim 1, wherein the composition comprises a methimazole derivative according to Formula (II), and wherein X is S.

11. The method according to claim 1, wherein the composition comprises a methimazole derivative according to Formula (III), and wherein X is S.

12. The method according to claim 1, wherein the subject is a mammal, and wherein the one or more methimazole derivatives is administered systemically.

13. The method according to claim 1, further comprising co-administering at least one of metformin, a thiazolidinedione, or an HMG-Co-A inhibitor.

14. A method for treating or reducing the risk of developing non-alcoholic fatty liver disease (NAFLD) in a subject in need thereof, the method comprising administering a composition comprising a therapeutically effective amount of one or more methimazole derivatives to the subject, wherein the one or more methimazole derivatives have a formula selected from (X) and (XI):

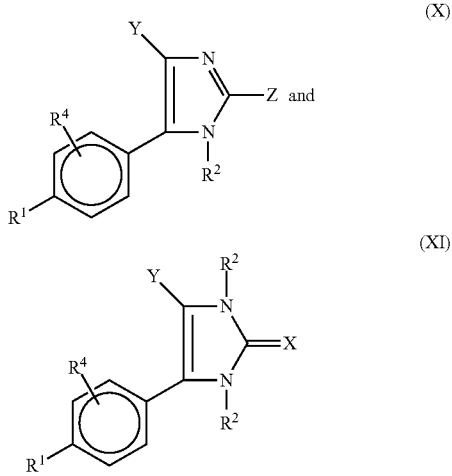

or pharmaceutically-acceptable salts or solvates thereof; wherein:
(a) Y is selected from H, C₁-C₄ alkyl, C₁-C₄ and substituted alkyl;
(b) R¹ is selected from H, OH, halogens, C₁-C₄ alkyl, C₁-C₄ substituted alkyl, C₁-C₄ ester, and C₁-C₄ substituted ester;
(c) R² is independently selected from H, C₁-C₄ alkyl, and C₁-C₄ substituted alkyl;
(d) R⁴ is selected from H, C₁-C₄ alkyl, and C₁-C₄ substituted alkyl;
(e) Z is selected from SR³ and OR³;
wherein R³ is selected from H, C₁-C₄ alkyl, C₁-C₄ substituted alkyl, and —CH₂Ph,
wherein Ph is phenyl;
(f) X is selected from S and O.

15. The method according to claim 14, wherein the composition comprises one or more methimazole derivatives according to Formula (X), and wherein the one or more methimazole derivatives have a formula selected from (XII) and (XIII):

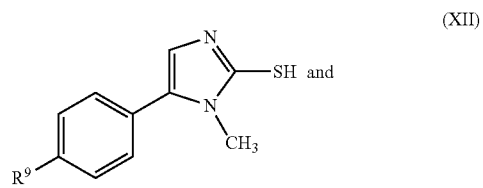

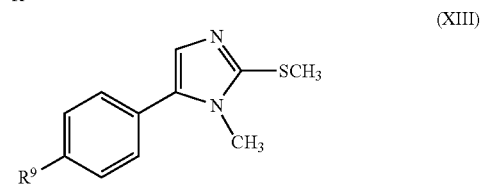

wherein R⁹ is selected from —OH, -M, and —OOCCH₂M; and wherein M is a halogen.

16. The method according to claim 14, wherein the composition comprises one or more of the following methimazole derivatives according to Formula (XI):

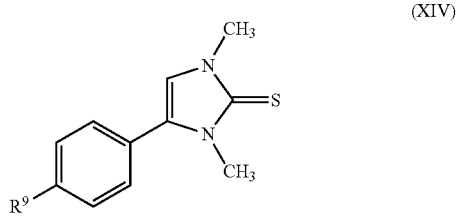

wherein R⁹ is selected from —OH, -M, and —OOCCH₂M; and wherein M is a halogen.

17. A pharmaceutical composition for treatment of or reduction of the risk of developing non-alcoholic fatty liver disease (NAFLD) comprising:
(a) a therapeutically effective amount of one or more of metformin, thiazolidinediones, or HMG-Co-A inhibitors; and
(b) a therapeutically effective amount of one or more methimazole derivatives having a formula selected from (I), (II), and (III):

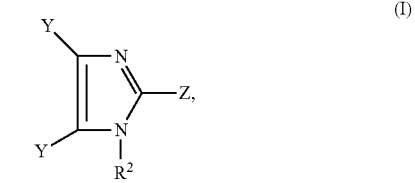

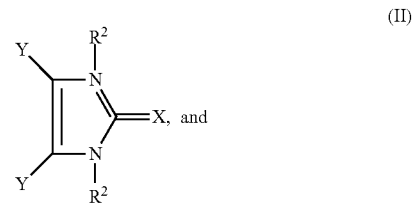

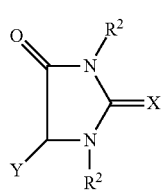

or pharmaceutically-acceptable salts or solvates thereof; wherein:
(i) Y is independently selected from H, $C_1$-$C_4$ alkyl, $C_1$-$C_4$ substituted alkyl, $NO_2$, and a phenyl moiety having Formula (IV):

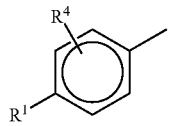

wherein no more than one Y of a methimazole derivative may be the phenyl moiety of Formula (IV); $R^1$ is selected from H, OH, halogens, $C_1$-$C_4$ alkyl, $C_1$-$C_4$ substituted alkyl, $C_1$-$C_4$ ester, and $C_1$-$C_4$ substituted ester; and $R^4$ is selected from H, $C_1$-$C_4$ alkyl, and $C_1$-$C_4$ substituted alkyl;
(ii) $R^2$ is independently selected from H, $C_1$-$C_4$ alkyl, and $C_1$-$C_4$ substituted alkyl;
(iii) Z is selected from $SR^3$, $S(O)R^3$, $OR^3$, and $C_1$-$C_4$ alkyl;
wherein $R^3$ is selected from H, $C_1$-$C_4$ alkyl, $C_1$-$C_4$ substituted alkyl, and —$CH_2Ph$,
wherein Ph is phenyl; and
(iv) X is selected from S and O.

18. The pharmaceutical composition according to claim 17, further comprising a pharmaceutically acceptable carrier.

19. A device comprising a reservoir of the pharmaceutical composition according to claim 17.

20. A method for treatment of or reduction of the risk of developing non-alcoholic fatty liver disease (NAFLD), the method comprising administering a therapeutically effective amount of the pharmaceutical composition according to claim 17.

* * * * *

UNITED STATES PATENT AND TRADEMARK OFFICE
CERTIFICATE OF CORRECTION

PATENT NO. : 9,750,723 B2
APPLICATION NO. : 15/032508
DATED : September 5, 2017
INVENTOR(S) : Kelly D. McCall et al.

It is certified that error appears in the above-identified patent and that said Letters Patent is hereby corrected as shown below:

On the Title Page

Insert:
--(60) Related U.S. Application Data
Oct. 31, 2013 .........................................61/898,110--;

In the Specification

Column 1, Line 45:
"drome), NAFLD is observed in up 75% of obese persons."
Should read:
--drome), NAFLD is observed in up to 75% of obese persons.--;

Column 10:

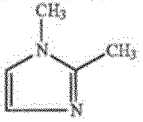

Signed and Sealed this
Twenty-fourth Day of July, 2018

Andrei Iancu
*Director of the United States Patent and Trademark Office*

CERTIFICATE OF CORRECTION (continued)

Should read:

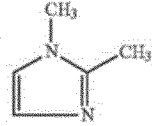

--;

Column 11:

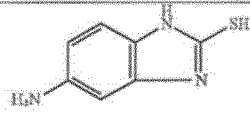

Should read:

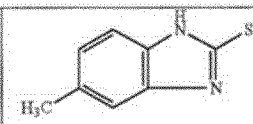

--;

Column 16, Line 48:
"NAFLD include co-administering with the phneylmethima-"
Should read:
--NAFLD include co-administering with the phenylmethima- --; and Column 25, Line 29:
"liver tissue from the C57BL/6J fed the LFD (*see e.g.*, FIG."
Should read:
--liver tissue from the C57BL/6J mice fed the LFD (*see e.g.*, FIG.--.